United States Patent
Al-Murrani et al.

(10) Patent No.: US 10,876,161 B2
(45) Date of Patent: Dec. 29, 2020

(54) PATTERN RECOGNITION RECEPTOR EXPRESSION AS A MEASURE OF SYSTEMIC HEALTH

(71) Applicant: Hill's Pet Nutrition, Inc., Topeka, KS (US)

(72) Inventors: Samer Al-Murrani, Topeka, KS (US); Dale S. Scherl, Lawrence, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 400 days.

(21) Appl. No.: 14/654,272

(22) PCT Filed: Dec. 20, 2012

(86) PCT No.: PCT/US2012/070936
§ 371 (c)(1),
(2) Date: Jun. 19, 2015

(87) PCT Pub. No.: WO2014/098865
PCT Pub. Date: Jun. 26, 2014

(65) Prior Publication Data
US 2015/0329908 A1    Nov. 19, 2015

(51) Int. Cl.
*C12P 19/34*    (2006.01)
*C12Q 1/6883*    (2018.01)
*G16B 25/00*    (2019.01)
*G16H 50/20*    (2018.01)

(52) U.S. Cl.
CPC ........... *C12Q 1/6883* (2013.01); *G16B 25/00* (2019.02); *G16H 50/20* (2018.01); *C12Q 2600/106* (2013.01); *C12Q 2600/158* (2013.01); *C12Q 2600/166* (2013.01); *Y02A 90/10* (2018.01)

(58) Field of Classification Search
None
See application file for complete search history.

(56) References Cited

U.S. PATENT DOCUMENTS

| | | | |
|---|---|---|---|
| 6,596,492 B2 | 7/2003 | Avery et al. | |
| 7,026,151 B2 | 4/2006 | Yamashita et al. | |
| 7,598,031 B2 | 10/2009 | Liew | |
| 7,873,482 B2 | 1/2011 | Stefanon et al. | |
| 2003/0206874 A1 | 11/2003 | Doyle et al. | |
| 2004/0022786 A1* | 2/2004 | Dedea | C07K 14/47 424/144.1 |
| 2004/0023870 A1* | 2/2004 | Dedera | C07K 14/47 424/133.1 |
| 2004/0136924 A1 | 7/2004 | Boyd et al. | |
| 2005/0158252 A1* | 7/2005 | Romanowski | A61K 8/345 424/49 |
| 2005/0163727 A1 | 7/2005 | Doyle et al. | |
| 2006/0024246 A1 | 2/2006 | Maitra et al. | |
| 2006/0116561 A1 | 6/2006 | Tricca et al. | |
| 2006/0127329 A1 | 6/2006 | Xu et al. | |
| 2006/0216357 A1* | 9/2006 | Cupp | A61K 35/20 424/535 |
| 2008/0260836 A1 | 10/2008 | Boyd | |
| 2009/0311142 A1 | 12/2009 | Burgess-Cassler et al. | |
| 2012/0231057 A1 | 9/2012 | Hack | |

FOREIGN PATENT DOCUMENTS

WO    WO-2011130646 A1 *    10/2011    ........... A61K 9/0014

OTHER PUBLICATIONS

Papapanou, PN. et al. Periodontal therapy alters gene expression of peripheral blood monocytes. J Clin. Periodontology, vol. 34, p. 736-747, 2007.*
Rojo-Botello, NR et al. Expression of toll-like receptors 2,4 and 9 is increased in gingival tissue from patients with type 2 diabetes amd chronic periodontitis. J. Periodont Res., vol. 47: p. 62-73, 2012, Epub Aug. 17, 2011.*
Dolieslager, SMJ. et al. The influence of oral bacteria on tissue levels of Toll-like receptor and cytokine mRNAs in feline chronic gingivostomatitis and oral health. Veternary Immunology and Immunopathology, vol. 151, p. 263-274, 2013. Epub Dec. 12, 2012.*
Ignacio et al. Toll-like receptor expression in feline lymphoid tissues. Veterinary Immunology and immunopathology, vol. 106, p. 229-237, 2005.*
Hofmann-Lehmann et al. Feline immunodeficiency virus (FIV) infection leads to increased incidence of feline odontoclastic resorptive lesions (FORL). Veterinary Immunology and immunopathology, vol. 65, p. 299-308, 1998.*
Beklen et al., 2008, "Immunohistochemical localization of Toll-like receptors 1-10 in periodontitis," Oral Microbiol. Immunol. 23:425-431.
Buduneli et al., 2011, "Salivary and plasma levels of toll-like receptor 2 and toll-like receptor 4 in chronic periodontitis," J. Periodontol. 82(6):878-884.
Correa et al., 2010, "Effect of periodontal treatment on metabolic control, systemic inflammation and cytokines in patients with type 2 diabetes," J. Clin. Periodontol 37:53-58.
Crasta et al., 2009, "Bacteraemia due to dental flossing," J. Clin. Periodontol. 36:323-332.
Cullinan et al., 2009, "Periodontal disease and systemic health: current status," Australian Dental J. 54(1 Supp):S62-S69.
(Continued)

*Primary Examiner* — Kenneth R Horlick

(57) ABSTRACT

The present invention encompasses methods and kits employing pattern recognition receptor expression as a measure of systemic health in a subject afflicted with an oral health condition. In particular, the present invention is directed to methods involving measurement of the expression levels of one or more Pattern Recognition Receptors including but not limited to Toll Like Receptors, myeloid differentiation primary response gene 88 (MyD88), and Nucleotide Binding oligomerization domain containing protein 1 (NOD1), in a companion animal, e.g., a dog or a cat, afflicted with an oral health condition. The described methods enable evaluation of the systemic health of the animal afflicted with an oral health condition by measuring expression levels of the indicated genes as compared to suitable controls.

25 Claims, No Drawings
Specification includes a Sequence Listing.

(56) References Cited

OTHER PUBLICATIONS

D'Aiuto et al., 2007, "Acute effects of periodontal therapy on bio-markers of vascular health," J Clin Periodontol. 34(2):124-429.
Debowes et al., 1996, "Association of periodontal disease and histologic lesions in multiple organs from 45 dogs," J. Vet. Dent. 13(2):57-60.
Deshpande et al., 1998, "Invasion of Aortic and Heart Endothelial Cells by Porphyromonas gingivalis," Infection and Immunity 66(11):5337-5343.
Forner et al., 2006, "Incidence of bacteremia after chewing, tooth brushing and scaling in individuals with periodontal inflammation," J. Clin. Periodontol. 33(6):401-407.
Gelani et al., 2009. "The role of toll-like receptor 2 in the recognition of Aggregatibacter actinomycetemcomitans," J. Periodontol. 80(12):2010-2019.
Gibson III et al., 2007, "Porphyromonas gingivalis mediated periodontal disease and atherosclerosis: disparate diseases with commonalities in pathogenesis through TLRs," Current Pharmaceutical Design 13(36):3665-3675.
Glickman et al., 2009, "Evaluation of the risk of endocarditis and other cardiovascular events on the basis of the severity of periodontal disease in dogs," J. Am Vet Med Assoc. 234(4):486-494.
Glickman et al., 2011, "Association between chronic azotemic kidney disease and the severity of periodontal disease in dogs," Preventive Veterinary Medicine 99(2-4):193-200.
Herzberg et al., 1996. "Effects of oral flora on platelets: possible consequences in cardiovascular disease," J. Periodontol. 67(10 Suppl):1138-1142.
Ide et al., 2003, "Effect of treatment of chronic periodontitis on levels of serum markers of acute-phase inflammatory and vascular responses," J Clin Periodontol. 30(4):334-340.
Ignacio et al., 2005, "Toll-like receptor expression in feline lymphoid tissues," Vet. Immunol. Immunopathol. 106(3-4):229-237.
International Search Report and Written Opinion in International Application No. PCT/US2012/070936, dated Aug. 2, 2013.
Jagannathan et al. 2009, "TLR cross-talk specifically regulates cytokine production by B cells from chronic inflammatory disease patients," J. Immunol. 183(11):7461-7470.
Janket et al., 2005, "Does periodontal treatment improve glycemic control in diabetic patients? A meta-analysis of intervention studies," J. Dent. Res. 84(12):1154-1159.
Jones et al., 2007, "Does periodontal care improve glycemic control? The Department of Veterans Affairs Dental Diabetes Study," J. Clin. Periodontol. 34:46-52.
Kawai et al., 2009, "The Roles of TLRs, RLRs and NLRs in Pathogen Recognition" International Immunology 21(4):317-337.
Kinane et al., 2008, "Group E of European Workshop on Periodontology. Periodontal diseases and health: Consensus Report of the Sixth European Workshop on Periodontology," J. Clinical Periodontol. 35(8 Suppl):333-337.
Lima et al., 2010, "The essential role of toll like receptor-4 in the control of Aggregatibacter actinomycetemcomitans infection in mice," J. Clin. Periodontol. 37(3):248-254.
Lockhart et al., 2008, "Bacteremia associated with toothbrushing and dental extraction," Circulation 117(24):3118-3125.
Logan, 1994, "Oral health assessment in dogs: parameters and methods," J. Vet. Dent. 11(2):58-63.
Mahanonda et al., 2007, "Toll-like receptors and their role in periodontal health and disease," Periodontol 2000 43:41-55.
Papapanou et al., 2007, "Periodontal therapy alters gene expression of peripheral blood monocytes," J Clin Periodontol. 34:736-747.

Pérez-Chaparro et al., 2008, "Genotypic characterization of Porphyromonas gingivalis isolated from subgingival plaque and blood sample in positive bacteremia subjects with periodontitis," J. Clin. Periodontol. 35:748-753.
Rawlinson et al., 2011, "Association of periodontal disease with systemic health indices in dogs and the systemic response to treatment of periodontal disease," J. Am. Vet Med Assoc. 238(5):601-609.
Rojo-Botello et al., 2012, "Expression of toll-like receptors 2, 4 and 9 is increased in gingival tissue from patients with type 2 diabetes and chronic periodontitis," J. Periodontal Research 47(1):62-73.
Sarah et al., 2006, "Expression of Toll-like receptors 2 and 4 in gingivitis and chronic periodontitis," Indian J. Dent. Res. 1.7(3):11.4-116.
Scannapieco et al., 2003, "Associations between periodontal disease and risk for atherosclerosis, cardiovascular disease, and stroke. A systematic review," Ann Periodontol. 8(1):38-53 Review.
Scannapieco, 1998, "Position paper of The American Academy of Periodontology: periodontal disease as a potential risk factor for systemic diseases," J. Periodontol. 69(7):841-850 Review.
Scannapieco, 2004, "Periodontal inflammation: from gingivitis to systemic disease?" Compend Contin Educ Dent. 25(7 Suppl 1):16-25.
Scannapieco, 2005, "Systemic effects of periodontal diseases," Dent Clin North Am. 49(3):533-250, vi. Review.
Silver et al., 1975, "Recovery and clearance rates of oral microorganisms following experimental bacteraemias in dogs," Arch. Oral Biol. 20(10):675-679.
Silver et al., 1977, "Experimental transient bacteraemias in human subjects with varying degrees of plaque accumulation and gingival inflammation," J. Clin. Periodontol, 4(2):92-99.
Sorensen et al., 2008, "Blood cell gene expression profiling in subjects with aggressive periodontitis and chronic arthritis," J. Periodontol. 79(3):477-485.
Stewart et al., 2001, "The effect of periodontal treatment on glycemic control in patients with type 2 diabetes mellitus," J. Clin. Periodontol. 28(4):306-310.
Takeuchi et al. 1999, "Differential roles of TLR2 and TLR4 in recognition of gram-negative and gram-positive bacterial cell wall components," Immunity 11(4):443-451.
Teng et al., 2002, "Periodontal healthand systemic disorders," J. Canadian Dental Assoc. 68(3):188-192.
Tonetti, 2009, "Periodontitis and risk for atherosclerosis: an update on intervention trials," J. Clin. Periodontol 36(Suppl. 10):15-19.
Written Opinion in International Application No. PCT/US2012/070936, dated Nov. 19, 2014.
Yamaguchi et al., 2009, "Ability of supragingival plaque to induce toll-like receptor 4-mediated stimulation is associated with cytokine production by peripheral blood mononuclear cells," J. Periodontol 80(3):512-520.
Yoshioka et al., 2008, "Analysis of the Activity to Induce Toll-Like Receptor (TLR)2- and TLR4-Mediated Stimulation of Supragingival Plaque," J. Periodontol. 79(5):920-928.
Bell, K. P. et al., "Dental hygienists' knowledge and opinions of oral-systemic connections: implications for education", J. Dent. Educ., Jun. 2012, 76:682-694.
Cave, N. J. et al., "Systemic effects of periodontal disease in cats", Vet. Q., 2012, 32:131-144, Published online Nov. 29, 2012.
Ramamoorthy, R. D. et al., "A review of C-reactive protein: A diagnostic indicator in periodontal medicine", J. Pharm. Bioallied. Sci., Aug. 2012, 4(2):S422-S426.
Scheres, N, et al., "Periodontal ligament and gingival fibroblasts from periodontitis patients are more active in interaction with Porphyromonas gingivalis", J. Periodontal. Res., 2011, 46:407-416.

* cited by examiner

SEQUENCE LISTING

<160> NUMBER OF SEQ ID NOS: 31

<210> SEQ ID NO 1
<211> LENGTH: 18
<212> TYPE: DNA
<213> ORGANISM: Felis catus

<400> SEQUENCE: 1
ggccctggac ctcagcta                                                 18

<210> SEQ ID NO 2
<211> LENGTH: 16
<212> TYPE: DNA
<213> ORGANISM: Felis catus

<400> SEQUENCE: 2
gacccacgcc ctgcat                                                   16

<210> SEQ ID NO 3
<211> LENGTH: 30
<212> TYPE: DNA

<213> ORGANISM: Felis catus

<400> SEQUENCE: 3
gaaaacctga ctatatcaga tgcacaaatg                                    30

<210> SEQ ID NO 4
<211> LENGTH: 31
<212> TYPE: DNA
<213> ORGANISM: Felis catus

<400> SEQUENCE: 4
agcaaaattt aaatgtttga atcttgtggg a                                  31

<210> SEQ ID NO 5
<211> LENGTH: 20
<212> TYPE: DNA
<213> ORGANISM: Felis catus

<400> SEQUENCE: 5
cacagtgttg ccgacatctc                                               20

<210> SEQ ID NO 6
<211> LENGTH: 21
<212> TYPE: DNA
<213> ORGANISM: Felis catus

<400> SEQUENCE: 6
ctcggtgatc agcaggaaga c                                             21

<210> SEQ ID NO 7
<211> LENGTH: 14
<212> TYPE: DNA
<213> ORGANISM: Felis catus

<400> SEQUENCE: 7
acggcgctgg ctga                                                     14

<210> SEQ ID NO 8
<211> LENGTH: 19
<212> TYPE: DNA
<213> ORGANISM: Felis catus

<400> SEQUENCE: 8
gctgccggat ctccaagta                                                19

<210> SEQ ID NO 9
<211> LENGTH: 20
<212> TYPE: DNA
<213> ORGANISM: Felis catus

<400> SEQUENCE: 9
gctctgctgc ttgtcaccat                                               20

<210> SEQ ID NO 10
<211> LENGTH: 23
<212> TYPE: DNA
<213> ORGANISM: Felis catus

<400> SEQUENCE: 10
ggcagtcaca gtaacagtca aca                                           23

<210> SEQ ID NO 11
<211> LENGTH: 21

```
<212> TYPE: DNA
<213> ORGANISM: Felis catus

<400> SEQUENCE: 11
actgactcct gggtcttttg c                                              21

<210> SEQ ID NO 12
<211> LENGTH: 18
<212> TYPE: DNA
<213> ORGANISM: Felis catus

<400> SEQUENCE: 12
ccactctgcg gagcatca                                                  18

<210> SEQ ID NO 13
<211> LENGTH: 23
<212> TYPE: DNA
<213> ORGANISM: Felis catus

<400> SEQUENCE: 13
tctctgattg tcagctggaa cag                                            23

<210> SEQ ID NO 14
<211> LENGTH: 26
<212> TYPE: DNA
<213> ORGANISM: Felis catus

<400> SEQUENCE: 14
aggtggttgt gactcatatt tagcaa                                         26

<210> SEQ ID NO 15
<211> LENGTH: 25
<212> TYPE: DNA
<213> ORGANISM: Felis catus

<400> SEQUENCE: 15
ctattcaaca gcgtttgagg agcta                                          25

<210> SEQ ID NO 16
<211> LENGTH: 28
<212> TYPE: DNA
<213> ORGANISM: Felis catus

<400> SEQUENCE: 16
tgccttctga ttgaaagtaa tggctatt                                       28

<210> SEQ ID NO 17
<211> LENGTH: 2958
<212> TYPE: DNA
<213> ORGANISM: Felis catus

<400> SEQUENCE: 17
tgcgactggc tgttcctcaa gtccgtgccc cacttctcgg cggcagcgcc ccgtggtaac    60
gtcaccagcc tttccctgta ctccaaccgc atccaccacc tccacgactc cgactttgtc   120
cacctgtcca gcctgcggcg tctcaacctc aaatggaact gcccaccgc cagcctcagc    180 cccatgcact tccctgtca catgaccatt gagccccaca ccttcctggc cgtgcccacc    240
ctggaggagc tgaacctgag ctacaacagc atcacgacag tacccgcct gcccagttcc    300 ctcgtgtccc tgtccttgag ccgtaccaac atcctggtgc tggaccctgc caacctcgca   360
gggctgcact ccctgcgctt tctgttcctg atggcaact gctactacaa gaaccctgc    420
```

```
ccgcaggccc tgcaggtggc cccgggcgcc ctccttggcc tgggcaacct tacgcacctg    480
tcactcaagt acaacaacct cactgcggtg ccccgcggcc tgcccccag cctggagtac     540 ctgctattgt cctacaacca catcatcacc ctggcacctg aggacctggc caacctgacc    600
gccctgcgtg tgctcgatgt gggtggaaac tgccgtcgct gtgaccacgc ccgcaacccc    660
tgtatggagt gccccaaggg cttcccgcac ctgcaccctg acaccttcag ccacctgaac    720
cacctcgaag gcctggtgtt gaaggacagc tctctctaca acctgaaccc cagatggttc    780
catgccctgg gcaacctcat ggtgctggac ctgagtgaga acttcctata tgactgcatc    840 accaaaaacca cagccttcca gggcctggcc cagctgcgca gactcaactt gtctttcaat    900
taccacaaga aggtgtcctt tgcccacctg catctggcgc cctccttcgg gagcctgctc    960
tccctgcagc agctggacat gcatggcatc ttcttccgct cgctcagcga gaccacgctc   1020
cggtcgctgg tccacctgcc catgctccag agtctgcacc tgcagatgaa cttcatcaat   1080
caggcccagc tcagcatctt cggggccttc cctggcctgc gatacgtgga cctgtcagac   1140
aaccgcataa gtggagccat ggagctggcg gctgccacgg ggaggtgga tggtggggag    1200 agagtccggc tgccatctgg ggacctagct ctgggcccac cgggcacccc tagctccgag   1260
ggcttcatgc caggctgcaa gaccctcaac ttcaccttgg acctgtcacg gaacaaccta   1320
gtgacaatcc agccagagat gtttgcccgg ctctcgcgcc tccagtgcct gctcctgagc   1380
cgcaacagca tctcgcaggc agtcaacggc tcacaattta tgccgctgac cagcctgcag   1440
gtgctggacc tgtcccataa caagctggac ctgtaccatg ggcgctcttt cacggagctg   1500
ccgcggctgg aggccctgga cctcagctac aacagccagc ccttcagcat gcagggcgtg   1560
ggtcacaacc tcagctttgt ggcacagctg ccggccctgc gctatctcag cctggcgcac   1620
aacgacatcc acgccgtgt gtcccagcag ctctgcagcg cctcgctgcg ggccttggac   1680
ttcagcggca atgccttgag ccggatgtgg gccgagggag acctgtatct ccgcttcttc   1740
cgaggcctga ggagcctggt ccggttggat ctgtcccaga atcgcctgca taccctcttg   1800
ccacgcaccc tggacaacct ccccaagagc ctgcggctgc tgcgtctccg tgacaattat   1860 ctggcttttct tcaactggag cagcctggtc ctcctcccca ggctggaagc cctgaccctg   1920
gcgggaaacc agctgaaggc cctgagcaac ggcagcttgc ctaatggaac ccagctccag   1980
aggctggacc tcagcagcaa cagtatcagc ttcgtggcct ccagcttttt tgctctggcc   2040
accaggctgc gagagctcaa cctcagtgcc aacgccctca gacggtgga gccctcctgg    2100 ttcggttctc tagcgggcac cctgaaagtc ctagatgtga ctggcaaccc cctgcactgc   2160
gcctgtgggg cggccttcgt ggacttcttg ctggaggtgc aggctgcagt gcccggcctg   2220
ccaggccacg tcaagtgtgg cagtccaggt cagctccagg gccgcagcat ctttgcgcag   2280
gatctgcgcc tctgcctgga tgaggccctc tcctgggact gttttggcct ctcgctgctg   2340
accgtggccc tgggcctggc cgtgcccatg ctgcaccacc tctgtggctg ggacctctgg   2400
tactgcttcc acctgtgcct ggcctggctg ccccggcggg gcggcggcg gggcgcggat    2460 gccctgccct acgatgcctt tgtggtcttc gacaaggcac agagcgcggt ggccgactgg   2520
gtgtacaacg agctgcgggt acggctagag gagcgccgtg gacgccgagc gctccgcctg   2580
tgcctggagg aacgtgactg gctacccggt aaaacgctct ttgagaacct gtgggcctca   2640
gtttacagca gccgcaagat gctgtttgtg ctggcccaca cagacaggt cagcggcctc    2700 ttgcgcgcca gctttctgct ggcccagcag cgcctgctgg aggaccgcaa ggacgttgtg   2760
gtgctggtga tcctgcgccc cgacgcccac cgctcccgct atgtgcggct cgccagcgc    2820
```

-continued

| | |
|---|---|
| ctctgccgcc agagcgtcct cctctggccc caccagccca gtggccagcg cagcttctgg | 2880 |
| gcccagctgg gcacgccct gaccagggac aaccagcact tctataacca gaacttctgc | 2940 |
| cggggcccca cgacggca | 2958 |

<210> SEQ ID NO 18
<211> LENGTH: 1780
<212> TYPE: DNA
<213> ORGANISM: Felis catus

<400> SEQUENCE: 18

| | |
|---|---|
| accaactgct ccaacatgtc ccttagaaag gttcatgcag acttgacccc aaccacaacc | 60 |
| acactggatt tatcctacaa cctccttct cagcttcaga gttcagattt tcgttctgtc | 120 |
| tctaaactga agttttgat tctgtgccac aacagaatcc aagagctgga tatcaagacc | 180 |
| tttgaattca acagagagtt aagatattta gatttgtctt acaacagatt gaagattgta | 240 |
| acttggtatt cactggcagg tctcagacat ttagatcttt cttcaatga ctttgacagt | 300 |
| gtgcctatcc acgaggaggc tggcaacatg tcacatctgg aaatcctggg tttgagtggg | 360 |
| gcaaaaatac gaaaatcaga tttccagaaa attgctcatt tgcatctaaa tacagtcttc | 420 |
| ttaggattaa gaagtctttc ttattatgaa gaaggtaacc tgcccatctt aaacacaaca | 480 |
| aaacttcata ttgttttacc aatgaacaca aatttctggg ttcttttgcg tgatggaatc | 540 |
| aagacttcaa aaatactaga aatgacaaac atagatggca aaagccaatt ttcaagttat | 600 |
| gaaactcaac aaaatcttac tttagcgaat tccaagacat ctattctatt gcttaataaa | 660 |
| gttgatttac tctgggacta ccttctcctc atcttccagt ttgtttggca tacatcagta | 720 |
| gaatgcttcc aagtccaaca tgtgactttt ggaggcaagg tttatcttga ccataattca | 780 |
| tttgattact caaatactgc aatgagagct ataaaattgg agcacataca gttcagaatt | 840 |
| ttttatattc cacaggaaag ggtctacttg cttttttacca aaatggatat agaaaacctg | 900 |
| actatatcag atgcacaaat gccacacatg cggtttccta attatcccac aagattcaaa | 960 |
| catttaaatt ttgctgataa tatcttaaca gatgacctgt ttaagcaacc tatccaattg | 1020 |
| cctcatttga aaactttaat tttgaagggc aataaattgg agacactttc tttagtgagt | 1080 |
| ttctttgcca acaacacatc cttgaagcac ttagatctca gccagaatct gttacaatat | 1140 |
| gaaaatgatg aaaattgctt ttggccagaa accttgatca ctatgaacct gtcatccaac | 1200 |
| aaatttgctg attctgtttt caggtgcttg cccagaagta ttcaaatact tgacctgaat | 1260 |
| aataacaaga ttcaaactgt ccctaaagag attattcatc tgaagtcttt gcgagaacta | 1320 |
| aatatcgcat ttaactttct aactgatctt cctgggtgca gtcatttcag aaaactctca | 1380 |
| attctgaaca ttgaaatgaa cttaattctc agcccatctc tggattttt ccagagctgt | 1440 |
| caggaagtta agactctgaa tgcaggaaga aacccattcc ggtgtacctg tgaattaaga | 1500 |
| gattttattc agctggaaaa atattcacag ggcatgatga ttggatggtc agattcatat | 1560 |
| atctgtgaat accctttgaa tctaaagggg actcggttaa aggatgttca tcttcctgaa | 1620 |
| ttatcttgca acacagctct gttgattgtc accattgtgg ttatcatgct agttctgggg | 1680 |
| actgctatgg ccttctgctg cctctacttt gatctgccct ggtatctcag gatgctaggt | 1740 |
| cagtggacac agacattgca gaggattagg aagacaaccc | 1780 |

<210> SEQ ID NO 19
<211> LENGTH: 1825
<212> TYPE: DNA

<213> ORGANISM: Felis catus

<400> SEQUENCE: 19

| | | |
|---|---|---|
| tgagccggta cacccagaag ctgcgacagc aactgggcct cgactccaag ttcatcctgt | 60 |
| gctacgccca gaaggaggag ctgttgctgg aggagctgta cacggacacc atcgtggagc | 120 |
| tggtgggctt caggaacgag agcctgggcc tgctgggcag cctggcctgc ctgctggacc | 180 |
| actccaccgg cgtcctcagc gagcaggcgc agaccatctt catcttcggg gacgccggcg | 240 |
| tgggcaagtc catgctgctt cagcggctgc agggcctgtg ggccgcgggg ctgctggagg | 300 |
| cggagttcaa gttcttcttc cacttccgct gccgcgtgtt cagctgcttc aaggaggacg | 360 |
| acgcgctgtg cctgcaggac ctgctcttta agcattactg ctacccggag caggacccgg | 420 |
| atgaggtgtt cgccttcctg ctgcgcttcc cccacacggc cctcttcacc ttcgacggcc | 480 |
| tggacgagct gcactcggac ttcgacctga gcagcgtgcc tgacacctcc tccccctggg | 540 |
| agcccgccca ccccctggcc ctgctggcca acctgctcag cgggaagctg ctcaagggcg | 600 |
| ccgccaagct gctcacggcc cgcacgggca tcgagatccc cgccagctc ctccgcaaga | 660 |
| aggtgtttct gcggggcttc tcgcccagcc agctgcgggc ctacacccag agggtgttcc | 720 |
| ccgagcccac cgtgcgggac cgcgtgctgg cccacctgga ggccaacccc aacctctgca | 780 |
| gcctgtgcgc cgtgcccctc ttctgctgga tcgtcttccg ctgtttccag cacttccaca | 840 |
| gtgttgccga catctccacg cagctgcctg actgcacggt gaccctgacc gacgtcttcc | 900 |
| tgctgatcac cgaggtccac ctgaacagga cgcagcccac cagcctggtc cagcggaaca | 960 |
| cgcgcagcca gacggagacc ttccgcgccg gggcgccgcc cttgcgctcg ctggggcggg | 1020 |
| tggcccacca gggcatggag aagaacctct ttgtctttgg ccaggaggac gtgcgggccg | 1080 |
| ccgaggtgca ggacggagag ctgcagctgg gcttcctgcg ggccgtgcca gagcagggcc | 1140 |
| tcggggtga ccagcaggcc tatgagtttt ccacgtcac cctccaggcc ttctttaccg | 1200 |
| ccttcttcct cgcggcggac gacaaggtag gcacgcagca gctgctcggg ttcttccggg | 1260 |
| agtgtgggct tcctggcgag gcggctgccg agtcctgcta cccctccttt ctccctgtgc | 1320 |
| ggtgtctgag gggccccggc ctggccgggg aggacctctt caagaacaag gatcacttcc | 1380 |
| agttcaccaa cctcttcctg tgcgggctgt tgtccaaggc caagcagaaa ctcctgcggc | 1440 |
| acctggtgcc cgccgcggtc ctgcggagaa agcgcaaggc cctgtgggcg cacctgtttg | 1500 |
| ccagcctgcg ggcccacctg aagagcctgc cccggctcca gtacgagggc tacaaccagg | 1560 |
| tgcaggccat gcccaccttc atctggatgc tgcgctgcat ctacgagacg cagagcgaga | 1620 |
| aggtggggcg gctggcggcc aagggcatct gtgcgaacta cctcaagctg acctactgca | 1680 |
| acgcctgctc ggccgactgc agcgccctct cgttcgtcct gcaccacctc cgcaagcggc | 1740 |
| tcgccctgga cctggacaac aacaacctca acgactacgg cgtgcgggag ctgcagccct | 1800 |
| gcttcagccg cctcacggtc atcag | 1825 |

<210> SEQ ID NO 20
<211> LENGTH: 334
<212> TYPE: DNA
<213> ORGANISM: Felis catus

<400> SEQUENCE: 20

| | | |
|---|---|---|
| cccgccatgg ccgccggagg ctcccgcgcg gggtccgcgt cccccatccc ctcggcgtcc | 60 |
| tccctgcctc tagctgccct caacgtgcga gtgcggcgcc gcctgtcgct gttcctgaac | 120 |
| gtgcggacgc aggtggcggc cgactggacg gcgctggctg aggagatggg cttcgagtac | 180 |

| | |
|---|---:|
| ttggagatcc ggcagctgga ggcgcatgcc gacccatgg gcaagctcct ggacgactgg | 240 |
| cagggacgcc cgggagcctc ggtgggccgt ctgctggagc tgctcaccaa gctgggccgc | 300 |
| gatgacgtgc tggtggaact ggggcccagc atcg | 334 |

<210> SEQ ID NO 21
<211> LENGTH: 1023
<212> TYPE: DNA
<213> ORGANISM: Felis catus

<400> SEQUENCE: 21

| | |
|---|---:|
| gaaggagatt gctcttggac tacaagttta ttaagtttaa atatgtcttc aaatatactt | 60 |
| acggactctg ttttcagatg tttacctcct aaggtcaagg tacttgatct tcacaataac | 120 |
| caaataagaa gcattcctaa accaatcatg aaactagaag ctttgcaaga actcaatgtt | 180 |
| gcctccaatt ccttagccca ccttcctgac tgtggagctt ttagcagcct ttctgtactg | 240 |
| atcattgacc ataattcaat ttccaaccca tcagctgatt tcttccacag ctgccagaag | 300 |
| attaggtcca taagagcagg aaacaatcca ttccaatgca cctgtgagct aagagaattt | 360 |
| atccagaata taggccaagc atcaagtgaa gtggtagagg gttggcctga ttcttataag | 420 |
| tgtgactatc cagaaagtta tagggaacc ccactaaagg actttcatgt gtctcagtta | 480 |
| tcctgcaaca cagctctgct gcttgtcacc attggggtca ctgtgctggt gttgactgtt | 540 |
| actgtgactg ccctctgtat gtactttgat ctgccctggt atctcaggat ggtgtgtcag | 600 |
| tggacccaga cccggcacag ggcaaggaaa ctacccttag aagaactcca agaacccttt | 660 |
| cagttccacg ctttatttc atatagtggg catgattctg tgtgggtgaa gagtgaatta | 720 |
| ttaccaaacc tagaaaaaga agacctaagg atttgtctcc atgagagaaa ctttgttcct | 780 |
| ggcaagagca ttgtggagaa tatcatcaac tgcattgaaa aaagttacaa gtccatcttt | 840 |
| gttttgtctc ccaactttgt tcagagtgag tggtgtcatt atgaactcta ctttgcccac | 900 |
| cacaatctat ttcatgaagg ttttgataac ttaattttaa tcttgctgga gcctattcca | 960 |
| cagtattcca ttcctagcag ctatcacaag ctcaaaaatc tcatggcacg aaggacttat | 1020 |
| ttg | 1023 |

<210> SEQ ID NO 22
<211> LENGTH: 2890
<212> TYPE: DNA
<213> ORGANISM: Felis catus

<400> SEQUENCE: 22

| | |
|---|---:|
| ggaatcatga gccagagttc gccttatatc tattcctttt tggggctgtt gcccttttgg | 60 |
| atactgtgta catcctccac caacaaatgt gttgttaggc atgaagcagc tgactgcagt | 120 |
| catctgaagt tgacacaagt gcccgatgac ctcccagcaa acataacggt gttgaatctc | 180 |
| acccataacc agctcagaag attaccgcct gacaacttta caagatatag ccaacttact | 240 |
| accttggatg gaggatttaa ctccatctca aaactggagc cagaattgtg ccaaaaactc | 300 |
| cccttgttgg aaattttgaa cctcgaacac aatgaactct ctcacctttc agagcgaact | 360 |
| tttatcttct gcgtgaattt gatggaactc catctaaggt ccaattcaat ccagaaaatt | 420 |
| gaaaacgatc ccttccaaaa cctgaagaat ttaatcaaat tagatctatc tcataatggt | 480 |
| ttgtcatcta ccaaattagg aagtcagctc caactgaaaa atctccaaga gctcctgtta | 540 |
| tcaaataata aaattaacag cctgagacgt gaagaactgg atttccttgg caattcttct | 600 |

```
ttgaagaaat tagaattgtc atcaaatcca attaaagagt tctctccagg gtgttttcat    660
gcaattggaa aactatttgg cctctctctg aacaatgctc aactgaaccc caacctcaca    720
gagcagcttt gtttagaact gtcgaacacg agcattcaga atctatcgct gagcaacacc    780
cagctgtaca gaacgagcaa tatgactttc gttgggctca agcacacaaa tctcaccgtg    840
ctcgatcttt cccacaacaa cttaaatgtg attgataatg gttccttcgt ttggcttcca    900
cgtctagaat atttcttcct ggggtataat aatatagaac acttatttc tcactccttg     960
tatgggcttc tcagtgtgag atacttggat ttgagacgat ctttcaccaa acaaagcact   1020
gctcttactt cgcgtcccaa gatcgatgat ttttcctttc agtggctaaa atgtttggag   1080
tatcttaaca tgggagacaa caacttccca ggcataagaa gcaatatgtt cacggggctg   1140
ataaagctga aacacttgag tctatccgac tccttcacaa gcttgcgaac tttaacaaat   1200
gaaacatttt tgtcacttgc tcagtctcct ttggtcacgc tcaacctaac caaaaacaaa   1260
atctcaaaaa tagagagtgg cgctttttct tgtctgggcc accttcaggt actcgacctt   1320
ggccttaatg aaattgggca agagctcaca ggccaagaat ggagaggtct aggaaatatc   1380
attgaaatct acctttccta caacaaatac ctacaactga ctcctgggtc ttttgccctg   1440
gttccaagcc tccaacgcct gatgctccgc agagtggccc tgagaaatgt ggacagttct   1500
ccttcacctt ttcattctct tcgcaacttg gtcattctgg atctaagcaa caacaatata   1560
gccaacataa atgataaact gttggagggt cttgagaaac tagaaattct ggaattgcag   1620
cacaacaact tagcacggct atggaaacgt gcaaacccta gtggtcctgt ttattttcta   1680
aagggtcttt ctcacctcca cattcttaac ttagagtcta atggctttga tgagatccca   1740
gcagaggtat tcaagggctt atctgaatta aagagcattg atttaggatt gaataattta   1800
aacatatttc cgctatctgt ctttgatgat caggcatctc taaagtcact gaaccttcag   1860
aagaatctca taacgtcagt tgagaaggat gttttttggggc cagccttcag gaacctgagt   1920
aatttagata tgagctttaa cccatttgat tgtacctgtg aaagtattgc ctggtttgtt   1980
aattggatta atagtaccca taccaacatc tctgacctgt caagccatta cctctgtaat   2040
actccacctc aatatcatgg tttcccggtg atgctttttg atatatcagc ctgcaaagac   2100
agtgcccect ttgaactctt tttcataata aataccagta tccttttgat tttcatcttt   2160
accgtattgc tcatccattt cgaaggctgg aggatatctt tttattggaa tgtttcagtg   2220
catcgagttc ttggtttcaa agaaatagac agacagccag agcagtttga atatgcagca   2280
tatataattc atgcctataa agatagagat tgggtctggg agaacttctc tccgatggaa   2340
gaaaagatc aaactctcag attttgtctc gaagaaggg actttgaggc aggtgtcctt   2400
gaacttgaat caattgttaa tagcatcaaa aggagcagaa aaactatttt cgttataacg   2460
cagcatctat taaaagatcc attgtgtaaa agattcaagg tgcaccaggc agttcagcaa   2520
gctgtggaac aaaatctgga ttccattata ttgatctttc ttgaggatat tccagattat   2580
aaactgaacc atgcactctg tttgcgacga gggatgttta atctcactg catcttgaac    2640
tggccagttc agaaagaacg ggtaaatgcc tttcatcata aattgcaagt agcgcttgga   2700
tccagaaatt caatacatta aatttattta aagactaagt taacaaaggc gtaactttcc   2760
cccacttaaa gagtttcata gtaaatttag gttttatttg aaaataatat acatctgttt   2820
attcagactt agagaggttt ctgataatta tatttggagt ttttttggga tgcactcata   2880
ggaaaataag                                                          2890
```

<210> SEQ ID NO 23
<211> LENGTH: 3113
<212> TYPE: DNA
<213> ORGANISM: Felis catus

<400> SEQUENCE: 23

| | | | | | |
|---|---|---|---|---|---|
| agaatgatgc | ctcctacccg | cctggctggg | actctgatcc | cagccatggc | cttcctctcc | 60 |
| tgcctgagac | ctgagagctg | ggacccttgt | gtggaggtgg | ttcctaacat | tacttaccaa | 120 |
| tgcatggacc | tgaatcttca | caaaatcccc | gacaacatcc | cctcatcaac | caaggacctg | 180 |
| gacatgagct | ttaaccccct | gagaaattta | ggcagccata | gtttctccaa | cttcccagaa | 240 |
| ctgcaggtgc | tggatttatc | caggtgtgaa | attcaaataa | ttgaagatga | tgcatatcag | 300 |
| ggcctaaacc | acctctccat | cttgatattg | acaggaaatc | ctatccagag | gttattccca | 360 |
| ggagcttttt | ctggactatc | aagtttacag | acgctggtgg | ctgtggagac | aaacatagca | 420 |
| tctctagagg | acttccccat | tggacatctc | aaaacgttga | aggagcttaa | tgtggctcac | 480 |
| aatcttatcc | attccttcaa | attacctgaa | tattttcta | acatgtccaa | ccttgagtat | 540 |
| ttggatcttt | ccaataacaa | gattcaaaat | atttatcata | aagacttaca | ggttctacat | 600 |
| caaaagcctc | tactcaacct | ttctttagac | ttgtccctca | acctttaga | ctttatccaa | 660 |
| ccaggtgcct | ttaagaagt | taagctccgt | gaactgactt | tgagaagtaa | ttttaatagt | 720 |
| acagatgtaa | tgaaagcttc | tattcaaggt | ctggcaggtt | tacagatcca | tcagttggtt | 780 |
| ctgggagaat | ttaaaaatga | aggaacttg | gaagatttga | caaatctat | cctggaggga | 840 |
| ctgtgcaatt | tgatcataga | aaaattccgg | atagcatact | ttgacaagtt | ctcagaggat | 900 |
| gctattgact | catttaattg | tttggcaaac | gtttctacca | tttctctggt | gcatctgtat | 960 |
| ttcaaggggc | taaacagct | ccctaaaaat | ctcggatggc | aacggttaga | attggttaac | 1020 |
| tgtgaatttg | aacaatttcc | cacatggaag | ctggaccctc | tcaaggagct | tgttttctcc | 1080 |
| gccaacgaag | ttaggaacgc | ttttactcag | gttaagttgg | aaagccttga | gtttctagac | 1140 |
| ctcagtagaa | atgactttag | tttgaagagt | tgctgttctg | agagagattt | ggggacaacc | 1200 |
| agactgaagc | atttagatct | aagcttcaac | aatattatta | ccataagttc | aaacttcttg | 1260 |
| ggcttagaac | agttagaata | tctagacttc | cagcattcca | gtttgaaaca | ggtcagtgat | 1320 |
| ttttcagtat | tcctacccct | caaaaacctc | cgttaccttg | atatttctta | cactcatacc | 1380 |
| caagttgcct | tccatggcat | cttcaatggc | ttgatcagcc | tccaaatctt | aaaaatggct | 1440 |
| ggcaattctt | tccaggacaa | cttccttcca | aatattttca | tggagctgac | taacttgacc | 1500 |
| attctagacc | tctctgattg | tcagctggaa | caggtgtccc | aagtggcatt | taactcactc | 1560 |
| cctaaacttc | agttgctaaa | tatgagtcac | aaccacctct | tatcattgga | tacacttcct | 1620 |
| tatgaacctc | ttcactccct | ccagactctg | gactgcagtt | ttaatcgtat | agtgcctct | 1680 |
| aaggagcaag | aactacggca | ttttccaagt | aatctatctt | ccttaaatct | tactcggaat | 1740 |
| gattttgctt | gtgtttgtga | acaccagagt | ttcctgcagt | gggtcaagga | ccagaggcag | 1800 |
| ctcttggtgg | aagttgaaca | gatggtgtgt | gcaaaacctt | tggacatgca | gggcatgccc | 1860 |
| atgctgaatt | ttaggaatgc | tacctgtcag | gtgagaaaga | ccatcattac | tgggtcggtt | 1920 |
| ttcactgtac | tcttggtttt | tctggtggtg | gttctggtgt | ataagttcta | tttccacctg | 1980 |
| atgcttcttg | ctggctgtaa | aaagtatagc | agaggtgaaa | gcacctatga | tgccttcgtt | 2040 |
| atctactcaa | gccaggatga | agattgggtg | aggaatgaat | tggtaaagaa | cttggaggag | 2100 |
| ggggtgcccc | cttttcagct | ctgccttcac | tacagagact | ttattcctgg | tgtggccatc | 2160 |

| | |
|---|---|
| gccgccaaca tcatccagga aggtttccat aaaagccgga aagttatcgt cgtggtgtcc | 2220 |
| cagcacttta tccagagtcg atggtgcatc tttgagtatg ggattgccca gacttggcag | 2280 |
| tttctcagca gccgtgccgg catcatcttc atcgtcctgc agaagttgga gaagtccctg | 2340 |
| ctgcggcagc aggtggagct gtatcgcctt ctcaacagga acacctacct ggagtgggag | 2400 |
| gacagtgtcc tggggaggca catcttctgg agacgactca gaaaagcctt gctggacggt | 2460 |
| aaaccacgct gtccagaagg aatggcagat gcagaaggca gctagcgtgg aagagtaacc | 2520 |
| tctgcctgag gaggaaacac tcctgcagtg cttcttgccc agctggaccc agtaccttcg | 2580 |
| ttcactaaat gagaattgaa tgctgtgaca tacctggcgc tgtgccaagg gcagatgatt | 2640 |
| cagtggtgcc cgaggaaccc aggactgctg acctcatggg gtttacagtg caggggagt | 2700 |
| aagtactgtg ctaaattaca gaatctccag gtggatgttt caaccaaatc agctaaggag | 2760 |
| tccatggcaa ggaaagtcaa ctcaacactt accccatcaa actgaattag acctaagacc | 2820 |
| ctgggcccta gtgaaatcag gagaaggtat agttcttcac ctgagtcttc tgaatggaaa | 2880 |
| ctacctcatg ttttacattt tagccagctt aaatttaact gaatgaggtc tttactcact | 2940 |
| tttcccttt ctattgaatg caatttaaat tccacttgat aactcagaag gctcctgatt | 3000 |
| gagaccacct cctctccaat ttcaacctgt ttccttacat aggctaaagt ctgtaactaa | 3060 |
| ttccgaagga aatctgagta atacatatcc acaaacaaaa aaaaaaaaa aaa | 3113 |

<210> SEQ ID NO 24
<211> LENGTH: 3706
<212> TYPE: DNA
<213> ORGANISM: Felis catus

<400> SEQUENCE: 24

| | |
|---|---|
| atttcatcgt ggaggaagac tgaacatggt gtttccaatg tgggcattga agagacagtc | 60 |
| ccttatcctt tttaacataa tcctaatttc caaactcctt ggagctagat ggtttcccaa | 120 |
| aactctgccc tgtgatgtca ctctggatgc tccaaaggcc catgtgattg tggactgcac | 180 |
| agacaagcat ttgacagaaa ttcctgaagg tattcctacc aatgccacca acctcaccct | 240 |
| caccatcaac cacataccctg gtatctctcc agcttccttc caccagctgg actacctggt | 300 |
| agagatcgat ttcagatgca actgtatacc tattcgactt gggccaaaag acaatatgtg | 360 |
| tcccaggagg ctgcagatta aacccagaag ctttagtaga ctcacttact taaaatccct | 420 |
| ttatctggat ggaaaccagc ttctagaaat acctgagggt cttccccca acttgcagct | 480 |
| gctgagcctt gaggccaaca gtatcttttg tatcatgaaa aataacctaa cagaactgac | 540 |
| caacatagaa aaactctact tgggccaaaa ctgttatttt cgcaatcctt gcaacgtttc | 600 |
| attttcata gaaaaagatg ctttcctgag tctgaaaaat ctaaaattgc tctccctaaa | 660 |
| agataacaat atcacatatg tccccactac attgccatcc actttaacag aactccatct | 720 |
| ttataacaac gccattgcaa aaatccaaga agatgatttt cataacctca atcaactgca | 780 |
| aattcttgac ctaggtggaa actgccctcg ttgttacaat gtcccatttc cttgtacacc | 840 |
| ctgtgagaac aattctcccc tacagatcca catgaaggct tttgatgcat tgacagaatt | 900 |
| acaagtttta cgtctataca gtaactctct tcagcatgtg ccccaaagat ggtttaaaaa | 960 |
| cattaaaaaa cttaaggagc tagatctttc acaaaacttc ttggccaaag aaattgggga | 1020 |
| tgccaaattt ttgcttcttc ttcacaacct tgtccaattg gatctgtctt tcaattatga | 1080 |
| acttcaggtc tatcgtgcaa ctctgaatct atcggatgca ttttcttcac tgaaaaacct | 1140 |
| gaaagtttta cggatcaaag gatacgtctt taaggagctg agcagccata acctctcccc | 1200 |

```
gttacgtagt ctctccaatc ttgaagttct tgatcttggc actaacttca taaaaatcgc    1260
tgacctcagc atattcgaac aatttaaaac attgaaagtc atagatcttt caatgaataa    1320
aatatcacct tcaggagatt caagtgaagt tggcttctgc tctaacacca gaacttctgt    1380
agatggtaat gcacctcagg tccttgaaac attacattat ttcagatatg atgagtatgc    1440
aaggagttgc aggttcaaaa acaaagagac tccctctttc ttgcctttta ataaagattg    1500
ttatgtgtat gggcaggcac tggacctaag tagaaataat atattttttg tcaagtcctc    1560
tgattttcag catctgtctt tcctcaaatg cctaaacttg tcaggaaata ccattggcca    1620
aactctcaat ggcagtgaat ttcagccttt agtggagttg aagtatttgg acttctttaa    1680
caaccggctt gatttactct attcaacagc gtttgaggag ctacgcaacc tggaaattct    1740
agatataagt agtaatagcc attactttca atcagaaggc attactcaca tgctaaactt    1800
caccaagaac ctaaaagttc tgaagaaact catgatgaac aacaatgaca tctctatgtc    1860
caccagcagg accatggaga gtgagtctct tagaattctg gaattcagag gaaatcattt    1920
ggatgtttta tggagagatg gtgataacag gtacttaaaa ttcttcaaga atctgctaaa    1980
cttagaggag ttagacatct ctgaaaaattc cctgagtttc ttgccttctg gcgttttga    2040 tggcatgcct ccaaaactaa agactctctc cttggtcaaa aatgggctca agtccttcaa    2100
ctggggaaga ctccagtatc tgaagaatct agaaactttg gacctcagct acaatgagct    2160
gaagagtgtc cctgagagat tatacaactg ttccagaagt ctcaagaaac tgattctcaa    2220
gtacaatcaa atcaggcatc tgacaaagca ttttctacaa gatgctttcc agttgcgata    2280
cctggacctc agctcaaata aaatccagat tatccagaag actagctttc cagaaaatgt    2340
cctcaataat ctgagagatg tacttttgca tcataatcgg tttctgtgca cctgtgatgc    2400
tgtgtggttt gtctggtggg ttaaccatac agaggtgact attccttact ggccacaga    2460 tgtgacttgt gtggggccag gagcacacag gggccagagt gtggtctctc tggatctgta    2520
tacctgtgag gtagatctga ctaacctgat cctgttttca ctttccgtat cggtggctct    2580
ttctctgatg gtgattacaa cagcaaacca cctctatttc tgggatgtgt ggtatagtta    2640
ccatttctgt aaggccaaaa taaaggggta tcagcgtctg acatcactgg attcttgcta    2700
cgatgccttt gttgtgtatg acactaaaga cccagcagtg acagagtggg ttttggatga    2760
gctggtggcc aagttggaag acccaagaga gaaacatttt aatctgtgtc ttgaggaaag    2820
ggattggcta ccagggcagc cagttctgga aaacctttcc cagagcatcc agcttagcaa    2880
aaagacggtg tttgtgatga caaacaagta tgcaaagacc gagaacttta agatcgcatt    2940
ttacttatcc catcagaggc tcatggatga aaaagtagac gtaattatct tgatattcct    3000
tgagaagccc cttcagaaat ccaagttcct ccagctccgg aagaggctgt gtaagagttc    3060
tgtccttgag tggccgacaa acccacaggc ccacccgtac ttctggcagt gtctgaaaaa    3120
tgccctggcc acagacaatc acgtgaccta tagtcaggtg ttcaaagaga cggtctagcc    3180
cttctttgcc cagcgtgact gcctgaccta ccaaggaaaa gcttggctgt ctagattgtc    3240
ccatgaatgc ctcactaaaa gggtgttgtt aaagtctcca agacctggga ttgtccacat    3300
cagagaggcg agtcacagtg tatgacaaag gaattggaaa aatggaattt ctataatgca    3360
tcacatcatc tttccgatct ctctgtgact ccattggcac ttgagtctcc cctttctgtt    3420
tctgtataag acacgactgg gagaagggcg gcaaggagag gacataaggc tctgattctc    3480
ctgtaattct cttgtgatta ttaaatacac acgcaatcac gaaattcaga ggaatcgtgc    3540
```

```
ttctactcct aagaagtacc gctctgtatg gaaataggat aaaagatgct cagggcctac    3600
gtgtatgaca tcacaatgta ccagagttag tgaaatgaaa acacagggaa cgcaactgat    3660
tgcttccgca tcacctagcg ccccttctg cacagatcga ctgttg                    3706
```

<210> SEQ ID NO 25
<211> LENGTH: 1253
<212> TYPE: DNA
<213> ORGANISM: Canis familiaris
<220> FEATURE:
<221> NAME/KEY: misc_feature
<222> LOCATION: (721)..(721)
<223> OTHER INFORMATION: n is a, c, g, or t

<400> SEQUENCE: 25

```
ccttcagcat gcggggcgtg ggccacaatc tcagctttgt ggcacagctg ccggccctgc      60
gctacctcag cctggcgcac aatggcatcc acagccgcgt gtcccagcag ctccgcagcg     120
cctcgctccg ggccctggac ttcagtggca atacccctgag ccagatgtgg gccgagggag    180
acctctatct ccgcttcttc caaggcctga gaagcctggt tcagctggac ctgtcccaga    240
atcgcctgca tacccctctg ccacgcaacc tggacaacct ccccaagagc ctgcggctcc    300
tgcggctccg tgacaattac ctggctttct tcaactggag cagcctggcc ctcctaccca    360
agctggaagc cctggacctg gcgggaaacc agctgaaggc cctgagcaat ggcagcttgc    420
ccaacggcac ccagctccag aggctggacc tcagcggcaa cagcatcggc ttcgtggtcc    480
ccagcttttt tgccctggcc gtgaggcttc gagagctcaa cctcagcgcc aacgccctca    540
agacggtgga gccctcctgg tttggttccc tggcgagtgc cctgaaagtc ctagacgtga    600
ccgccaaccc cctgcattgc gcttgcggcg caaccttcgt ggacttcttg ctggaggtgc    660
aggctgcggt gccggcctg cctagccgtg tcaagtgcgg cagacccggt cagctccagg    720
nccgcagcat cttcgcacag gacctgcgcc tctgcctgga cgaagcgctc tcctgggtct    780
gtttcagcct ctcgctgctg gctgtggccc tgagcctggc tgtgcccatg ctgcaccagc    840
tctgtggctg ggacctctgg tactgcttcc acctgtgcct ggcctggctg cccggcggg     900 ggcggtggcg gggtgtggat gccctggcct atgacgcctt cgtggtcttc gacaaggcgc    960
agagctcggt ggcggactgg gtgtacaatg agctgcgggt acagctagag gagcgccgtg    1020
ggcgccgagc gctacgcctg tgtctggagg aacgtgactg ggtacccggc aaaaccctct    1080
ttgagaacct ctgggcctca gtttacagca gccgcaagac gctgtttgtg ctggcccgca    1140
cggacagagt cagcggcctc ctgcgtgcca gcttcctgct ggcccaacag cgcctgctgg    1200
aggaccgcaa ggacgtcgtg gtgctggtga tcctgtgccc cgacgcccac cgc           1253
```

<210> SEQ ID NO 26
<211> LENGTH: 2368
<212> TYPE: DNA
<213> ORGANISM: Canis familiaris

<400> SEQUENCE: 26

```
ggacaatgtc acgtgttttg tggacattgt gggttttggg ggctgtaacc aacctctcca     60
aggaagaggc ccctgaccag tcttcttctc tgtcctgtga ccccactggt gtctgcgatg    120
gccgctccag atctttgaac tccatgccct cagggctcac agcagctgtg agaagccttg    180
acctctccaa caatgagatc acctacattg gcaacagtga ccttcgggat tgtgtgaacc    240
tcaaggctct gaggctggag tctaatggaa ttaacacaat agaggaagaa tcttttttttt    300 ccctgtggag tcttgaacat ttggacttat cttataacct cttatctaac ttatcatcct    360
```
cctggttcag gccccttct tcattgaagt tcttaaacct actgggaaat ccttacaaat        420
cacttgggga aacacctctt ttttctcagc tcacaaatct aagaattctg aaagtaggaa        480
atatctacag cttcactgag attcaggata aggattttgc tgggctaacc tttcttgagg        540
aactggagat cgatgcttca aatctccaga ggtatgagcc aaagagtttg aaatcgattc        600
agagcatcag ctatctggcc ctccgtatga agcagcctgt tttactggtg agattttg          660 tagatctttc cagttccttg aaacatttag aactgagaga tactcatttg acactttcc         720 acttttcaga ggcatccatc aatgaaacac atacgttggt taaaagtgg acatttagaa         780 atgtgaaagt caccgataga agttttactg aggttgtgag actgttgaat tatgtttctg        840
gagtgttaga agtagagttt gaggactgta cccttttatgg gctcggtgat tttgacatac       900
ctgatgtgga caaaattaaa aatataggtc agatagagac actaacagta cggaggttgc       960
atattccaca cttttactca ttttacgata tgagtagtat atattcactt acagaagatg      1020
ttaaaagaat cacagtagaa agcagtaagg tctttctggt tccttgctca ctttcacaac       1080
atttaaaatc cctagaatat ttggatctca gcgacaattt agtggttgaa gaatacttga       1140
gaaactcagc ctgtcagcat gcttggcccc tcctgcaaac cttaatttta aggcaaaatc       1200
gtttgaaatc cttagagaaa actggagaaa ctttgcttac tttgaaaaac ctggtgaacc       1260
ttgatattag taagaataat tatctttcta tgcctgaaac ttgtcagtgg ccagaaaagc       1320
tgaaatgttt gaacttatcc gacacaagaa tgcaaagtat aacccgttgc atccctcaga       1380
cactggaaat tttagatgtt agcaataata atctcgagtc attttccctg attttgccac        1440
aacttaaaga actttctatt tccagaaata agttgaagac tctaccagat gcctccttct       1500
tacccaccct acaaattatg agaatcagca gaaacacaat aaacgctttc tcgaaggagc       1560
aactggattc ctttcacagg ctgcagaccc tggaggccgg tggcaacaac ttcctttgct       1620
cctgtgaatt cctgtctttc actcaggagc agcaggccct ggccgggctc ctggtcggct       1680
ggccagagga ctacctgtgc cactcccct cctacgtgcg gggccagcgg gttgggaccg       1740
cccggctccc ggcttctgag tgccaccgga cagctctggt ggccgccgtg tgctgtgtct       1800
tgctcctgct ggtcctgctc acggcggggg cgtgccacca tttccacggg ctgtggtacc       1860
tgagaatgct gtgggcctgg ctccaggcca aaggaagcc caggaaagcc cctccaggg       1920 acgtctgtta tgacgccttt gtgtcttaca gtgagcatga ttcctactgg gtggagaacc      1980
ttctggtcca gaagctggag cacttcaatc ccccgttcaa gttgtgcctt cacaagcggg       2040
actttattcc cggcaagtgg attattgaca atatcattga ctccatcgag aagagccaca       2100
aaaccatctt tgtgctttct gaaaacttcg tgaaagcga gtggtgcaag tacgagctgg       2160
acttctccca ttttcgcctc tttgatgaga caacgatgc tgccatcctc attcttctgg       2220
agcccattga gaaaaggcc atccccacage gattctgtaa gctgcggaag ataatgaaca       2280
ccaagacgta cctggagtgg cccaccgatg atgctcagca ggaagggttt tggttaaatt       2340
tgagaacagc aataaaatcc tagattcg                                          2368

<210> SEQ ID NO 27
<211> LENGTH: 2709
<212> TYPE: DNA
<213> ORGANISM: Canis familiaris

<400> SEQUENCE: 27
aaaaactaac atctctagag gatttcccca ttggacatct caaaaccttg aaggagctta        60

-continued

```
atgtggctca caatcaccat tccttcaagc cacctgcgta tttctctaac atgcccaacc    120
tggagaacgt ggtatctttc caataacaag atccaaaata tttatcgtga agacttgcag    180
gatatctgca tcacatgcca ctactcaacc tttctttaga cttgtccctg aacccttat    240 actttatcca accaggttcc tttaaagaaa ttaaactcca taaactgact ttgagaagta    300
attttaatag tacagatgta atgaaaactt ttattcaaag tctggctggc ttaaagatca    360
atcagttggt tctgggagaa tttaaaaatg aaaggaagtt ggaaagcttt gacaattctc    420
tcctggaagg actgtgcaat tgaccattg aaaaattccg atagcatac tttgatagct      480 tctcaaagga tactactaac ttatttaacc agttggtaaa catttctgca atttctttgg    540
cgcatctgta tttagacaca ccaaaatacc ttcctaaaaa tctcagatgg caacggttgg    600
aaatagttaa ttgtaactta gaacaatttc ccgcatggga gctggactct ctcaaggagt    660
ttgttctcac ttccaacaaa ggtatgaaca cttttgctga tatgaagatg gaaagccttg    720
agtttctaga tctcagtaga atcgcctga gtttcaagac ttgctgctct cactctgatt     780
ttgggacaac cagactgaag catttagatc tgagcttcaa tgaaatcatt accatgagtt    840
caaacttctt gggcttagaa caactggaat atctagattt acagcattcc agtttgaagc    900
aggccagtga ttttcagta ttcttgtccc tcagaaacct ccgttacctt gatatttctt     960
atactcgcac tgaagttgct ttccagggca ttttttgatgg cttggtcagc ctcgaagtct   1020
tgaaaatggc tgataattcc tttccggaca actcccttcc aaatatttac aaagggttga   1080
ctaacttaac cattctggac ctttctaggt gtcatctgga acgggtgtcc caggaatcat   1140
ttgtctcact tcctaaactt caggtgataa atatgagtca caatagcctc ttgtcattgg   1200
atacactagc ttatgaacct ctcctctccc tccagatcct agattgcagt tcaatcgaa    1260 tagtagcctt caaggaacaa ggacaacagc attttccaag taatctagtt tccttaaatc   1320
ttactcggaa tagctttgct tgtgactgtg aacatcagag tttcctgcag tgggtcaaag   1380
accacaggca gctcttggtg aaagttgaac aaatggtgtg tgcaaaacct ttagacatga   1440
aggacatgcc cttgctaagt tttaggaatg ccaccctgtc agaggaagca agactatcaa   1500
ttagtgtgtc agttttcact gtgcttcatg gtttctctgg tagcagtttt agccggtata   1560
agttctattt tcacctgatg cttctcgctt ggcttgcaaa aggtataaca gaggggaaag   1620
tacctatgat gcattttgtt atctactcaa gccaggatga agactgggtg aggaatgaat   1680
tggtaaagaa cttggaggag ggagtgcccc cctttcagct ctgccttcac tacagagact   1740
tcattcctgg tgtggccatc gccgccaaca tcatccagga aggcttctac aaaagccgga   1800
aggttattgt tgtggtgtcc caacacttca tccagagtcg atggtgcatc tttgagtatg   1860
agattgccca gacttggcag tttcttagca gtcgtgctgg catcatcttc attgtcctgc   1920
agaaggtgga gaagtccctg ctgcggcagc aggtggaact gtatcgcctc tcagcagga    1980 acacttacct ggaatgggaa gacagtgtcc tggggcgcca catcttctgg agacggctcc   2040
gaaaagcctt gctggatggt aaaccgtgga gtccagaagg aacagaggat gcagaaaaaa   2100
gctagcatga agcaggaaac tctgcttgag gatgaaaagc tcctgtggtg cttcttgccc   2160
agctggaccc agtacttgtt cagttagcga tgtacctgcc actgtgctaa gggcggatga   2220
ttcagtggtg cacgagggct gcaggatgcc aacctcatgg agtttacagt gcagagggaa   2280
taaagctgtg ctaaaccaca gaacctccag gtggatgctt ccaccaaatc agctgaggag   2340
tccatggctg agtccatgga aagtcaactc aattcttacc ccatcaaact gagttggaac   2400
taggagactg ggtcccagag agatcaggga agagatatag ttcttcaact gagtctctgg   2460
```

| | |
|---|---|
| agtggaaact acctcatgac atgctagctc tctgaaagct gtttgggcag ttttaactga | 2520 |
| accaggtctt tgcccacttt tcccttttct attgaatgca attgaaattc gcttgatga | 2580 |
| ctcaaaagga tcctgattca gatcccttcc ccactactct aagccagttt ccttacaaag | 2640 |
| gctaaataaa gtctagcaac tagttccaaa ggaattctga ttaacgcaaa aaaaaaaaa | 2700 |
| aaaaaaaaa | 2709 |

<210> SEQ ID NO 28
<211> LENGTH: 4244
<212> TYPE: DNA
<213> ORGANISM: Canis familiaris

<400> SEQUENCE: 28

| | |
|---|---|
| aaacccctga accaccgagg tccccacagc ccctctgctc tgctctcttc aaccagactt | 60 |
| ctgtatttca cggtggaaga agactaaaaa tggtgtttcc aatgtggaca ttgaagagac | 120 |
| agttctttat ccttttgaac ataatcctga tttccaaact ccttggagcc agatggtttc | 180 |
| ctaaaactct gccctgtgat gtcagcctgg atgctccgaa ggcccatgtg attgtggact | 240 |
| gcacggacaa gcacctgacg gaaatcccgg gaggtattcc ctccaacgcc accaacctca | 300 |
| ccctcaccat taaccacata cccggcatct ctccagcctc cttccaccag ctggactatc | 360 |
| tggtagagat cgatttccga tgcaactgta tacctgttcg actggggccg aaagaccatc | 420 |
| tgtgcaccag gaggccacag attaaaccca gaagctttag cagcctcact tatttgaaat | 480 |
| cccttatct ggatggaaac cagcttctag aaataccga gggtcttcct cccagcttgg | 540 |
| agctgctgag cctcgaagcc aacagtatct tctctatcat gaaatataac ctaacagaac | 600 |
| tgaccaacat agaaaggctc tacttgggcc aaaactgtta ttttcgcaat ccttgtaatg | 660 |
| tttcattttt catcgaaaaa gatgctttcc taagtctgaa aaatctaaaa ttgctctccc | 720 |
| tcaaagataa caacatcacg tatgtcccta ctactttgcc gtctacttta acagaactct | 780 |
| acctttataa caacgccatt gcaaaaatcc aagaagatga ttttaataac ctcaatcaac | 840 |
| tgcgcatact cgacctaagt ggaaattgcc ctcgttgtta caatgtccca tttccttgca | 900 |
| caccctgtga aaataattcg cccctacaga tccatgagtc agctttcgat gcattgacag | 960 |
| aattacaggt gttacgtcta cacagtaact ctcttcagcg tgtgccccag agatggttta | 1020 |
| aaaacattaa aaagctcaag gagctcgatc tgtcccaaaa cttcttggcc aaagaaattg | 1080 |
| gggatgccaa attttgtat cttcttcacg accttgtcca actggatcta tctttcaatt | 1140 |
| atgaacttca ggtctatcgt gcagctctga tctgtccga gcgttttct tcactgaaaa | 1200 |
| acctgaaagt gttgcgcatc aaaggatacg tctttaagga gctgagcagc catcatctct | 1260 |
| ctccgttaca gagccttacc aatctcgaag ttcttgatct cggcactaac ttcataaaaa | 1320 |
| ttgcggacct cagcatattt gaacaattta aaacactgaa agtcatagac ctttcgatga | 1380 |
| ataagatatc cccttcagga gattcaggtg aagttggctt ctgctctagc accagaacct | 1440 |
| ctgtcgaagg tcatgcgcct caggtccttg agacattaca ttatttcaga tatgacgagt | 1500 |
| atgcaaggag ttgcaggttc aaaaacaaag agactccttc tttcttgcct tttaacaaag | 1560 |
| attgttacat gtatgggcag accctggacc taagtagaaa caacatcttt tttatcaagt | 1620 |
| cctctgattt tcagcatcct tctttcctca aatgcctaaa tttgtcagga ataccattg | 1680 |
| gccaaactct caatggcagt gaatttcagc cactagtgga gctgaaatac ttggacttct | 1740 |
| ctaacaaccg gcttgattta ctctactcga cggcatttga ggagctacgc aaactggaag | 1800 |

```
ttctagatat tagcagtaac agccattact ttcaatcaga aggaatcact cacatgctaa    1860
acttcaccaa gaacctaaaa gttctgaaga aactgatgat gaacaacaat gacatcgcta    1920
cgtccaccag caggaccatg gagagtgagt ctcttaaaat tctggaattc agaggaaatc    1980
atttggatgt tttatggaga gatggtgata acagatactt aaagttcttc aagaatctgc    2040
tgaacttaga ggaattagac atctctgaaa attccctgag cttcttgcct tctggagtgt    2100
ttgatggcat gcctccgaat ctaaagactc tctccttggt caaaaatggg ctcaagtcct    2160
ttcactggga aagactccag tatctgaaga atctagagac tttggacctc agctacaatg    2220
agctgaagat tgtccctgag agattataca actgttccag aagcctcaag aagctgattc    2280
ttaagtataa tcaaatcagg cagctgacaa agcattttct acaagatgct ttccagttgc    2340
gatatctgga cctcagctca aataaaatcc agattatcca gaagactagc tttccagaaa    2400
atgtcctcaa caacctggag atgttacttt tgcatcataa ccggtttctg tgcacctgtg    2460
atgctgtgtg gtttgtctgg tgggtcaacc acacagaggt gactattcct tacttggcca    2520
cagatgtgac ttgtgtgggg ccaggagcac acaagggcca gagtgtggtc tccctggatc    2580
tgtatacctg tgagttagat ctgactaacc tggttctgtt ctcatttttcc ctatcgctgg    2640
cccttttttct gatggtgatt acaacagcaa accacctcta cttctgggac gtgtggtaca    2700
gttaccatta ctgtaaggcc aaaataaagg ggtatcggcg tctgaaatca ctggactctt    2760
gctatgatgc tttcgttgtg tatgacacta agacccagc agtgaccgaa tgggttttgg    2820
atgagctggt ggccaagctg gaagacccaa gggagaaaca tttcaattta tgtcttgagg    2880
aaagggattg gttaccaggg cagccagttc tggaaaacct ttcccagagc atacagctta    2940
gcaaaaagac ggtgtttgtg atgacgaaca gtatgcaaa gaccgagaac tttaagatag    3000
cattttactt gtcccatcag aggctcatgg atgaaaagt ggacgtcatt atcttgatat    3060
tccttgagaa gccccttcag aaatccaagt cctccagct ccgcaagagg ctctgtaaga    3120
gttctgtcct ggagtggcca agaaacccac aggctcaccc atacttctgg cagtgcctga    3180
aaaatgccct ggccacagac aatcatgtga cctacagcca ggtgttcaaa gagacggtct    3240
aggccttctt tgcaaaatgg ggctgcctga ctcaccaagg agaagcttgg ctgcctagat    3300
tttctcttcg atgtctcact agaagggtgc tcgtaaattc tctaagaccc gggatggccc    3360
atagcagaga ggctggtgga agttggaaaa tggaatttat atgatacatc gagtcatctt    3420
acttatctct ctgtgactcc atttgcactg gagcctctcc tctctgttcc tggatagatg    3480
ctattgggag gacggcggca aggagaggac acgaggctct gactctcctg taatcctcta    3540
gtgattatta aatagacgtg caatcacaga ctactgagaa gaattgcact tcttcccgaa    3600
gaagaactac tggtatgtgt caaaaacgct cggggcctgc gtacaggaca ttaaaatgta    3660
gcagagtttg tgaaatgaaa acccagtcaa ctcgtcacct gatggcttct ttctgtgcag    3720
acccagagct ggctccccac ggaggattgc ctacgtgcca ctgtctcttc gcccttgggc    3780
ctgttgctgg gtccctggtg gaaatagtga gaaacaccct taccactggt gggcttggcc    3840
tacttacaaa tggaaaaaaa ttgaagctga tctgccttta tacaaatgag gctctttacc    3900
cttgatgata actcacctgc tcaagtattg ttacggactg aacgtctgtt ccctcccaaa    3960
ttcagatgtt gaagtgccaa ctcccagtgg gatggtgtca ggaggtggcc tttgggggg    4020
tgatcaggcc acgagggtgg agcctgcagg aatgggatca gtgctttatc agaagatagc    4080
agagggacgc cagggtggct caggggttga gcatctgcct ttggcccagg gcgtgatccc    4140
ggggtcccag gatggagtcc cgcttcgggc tccccgcagg gagcccgcct ctccctctgc    4200
```
ccgtgtctct gcctctctct gtgtctctca tgaacaaata aata 4244

<210> SEQ ID NO 29
<211> LENGTH: 2931
<212> TYPE: DNA
<213> ORGANISM: Canis familiaris

<400> SEQUENCE: 29

| | | | | | |
|---|---|---|---|---|---|
| atggggttca | gtgagggatg | tggaggtggg | ggtgggtcct | cgctgctccg | ggtgggccct | 60 |
| gccaccatca | cgagggtctt | cacgagctgg | gggctgcagg | gtcggctgga | gagggtggat | 120 |
| gaagcgtcgg | ggccacgcgg | cctggcgggc | cttgcctccc | tgggtgcgtc | cgaggccgca | 180 |
| cagtcctgct | gctcctgtca | agggccggcg | cccgtgctcc | agcttgggga | tggggagtgg | 240 |
| gtccctggc | cagctccctg | gtccctcgtg | agtgaccctg | gggggccctc | gggctctcga | 300 |
| gccatcagcg | tcatcatccg | agaccagctc | ccacgatctg | gagcaaagat | tttgttcgcg | 360 |
| acccgccgcg | cccggatctc | agatctccgc | gccctggcgc | tcctggttcg | cgcctccccc | 420 |
| agcgctgcgc | tccccagcca | ggtggccccg | tggatcgatc | tctcatccat | tatccccccc | 480 |
| aactgcaccg | tgagctctgc | aaggactgaa | gacctgtgcg | tcgtgggcca | caacagcacc | 540 |
| tgcaacagct | ctttgcacat | ggtaggtcct | ccacgaatat | ttgcccagcg | cattgcgaga | 600 |
| ggaggagagg | aaggagtggg | cgttctgttc | acaaacgacg | aacccgacct | aagtgggttc | 660 |
| cacaggctgg | caggggcaga | gcgaggcccc | caccccgtgg | gtgcttccat | cccaccaggt | 720 |
| gcccgctgtg | cagggtgcgc | agtggacttt | ggccaggagg | ccttggacgg | gggtgcagaa | 780 |
| tgcaacccgg | caggtctgcc | gcagcatccc | ccatgggact | cggtatggct | gcacctacct | 840 |
| gtgcccatgg | cctgcgcgga | cctgtcgctc | tccagcgcct | ttgacattct | aggtgccgca | 900 |
| ggccaggaca | agctcttgcg | tcttaagcac | aagctaaaga | ccctgcgcct | gggctgccgg | 960 |
| ggggcagacc | tcctgcacgc | catggtgctc | ctgaagctgg | gccgggagac | ggaggccagg | 1020 |
| atctccctgg | aagcactgaa | ggcggacgcg | gtggcccggc | ttgtggcgca | ccagtgggcc | 1080 |
| ggcatggatg | gtgccgaggc | ccccaaggag | ccaccagact | tgtcctgggc | agttgcccgg | 1140 |
| gtgtaccacc | tgcttaccga | ggagaacctg | tgccccgcca | cgatgcggga | cctggcctac | 1200 |
| caggcggccc | tccggacctt | cagctctagg | gatgaccacc | ggctggccga | gctccaggga | 1260 |
| gaggcccggg | accggtgtgg | gtggggcatc | gtcggggacc | cggggagctt | ccagcccctt | 1320 |
| cactccgatc | tgggctgcct | cccagcatcc | tcagtgtcac | cctcaggcgc | ccgcagcctt | 1380 |
| ccaaagccca | tagaggaccc | ctcggcctgg | agccgaggcc | gttccctgag | atccaccggc | 1440 |
| agcccagcct | ccctggccag | caatctggaa | atcagcgagt | cgcccaccat | gccctttctc | 1500 |
| agccgtcacc | gcagctgcca | tgaacccagc | aagctgtgcg | acgagcccca | ggccagcctg | 1560 |
| gtgcccgagc | ctgcccccac | gggctgccag | gagcctgagg | aggtgagctg | gccaccatca | 1620 |
| gaagagactg | ccagcccccc | accagaggag | acggccatcc | ccacgccgcc | tcctgacgtg | 1680 |
| gtcccagatg | caagcctcag | tgaccagctc | gaccccccca | aagcggggca | gatgggcacc | 1740 |
| cactaccccg | tggaatgcac | tgaaatgttg | gcagccccca | gctctctgtc | cttgccctct | 1800 |
| ggaaatgctc | gccctgtcaa | ggaccagacc | ccactcccac | ttcctgtaga | agacaccgct | 1860 |
| tcccagttgc | ccaaccccag | cccacctcct | ccctcagccc | tgaggacgtc | ccctccctgc | 1920 |
| ccttttccat | ccacctctcc | ttccactggc | ccggtcccct | cgcaccccctg | tccaccttct | 1980 |
| ccaaattctc | ccgaattgga | gtcggaacag | aaattctata | actttgtgat | cctgcacgcg | 2040 |

-continued

| | | |
|---|---|---|
| gcggcggacg agcacatcgc cctgcgggtc cgggagcggc tggaggccct gggcgtcccc | 2100 |
| gacggtgcca ccttctgcga ggacttccag gtgcccgggc ggggcgagct gcgctgcctg | 2160 |
| caggacgcca tcaaccactc ggccttcacc atcctgctgc tcaccccaa cctcaactgc | 2220 |
| cgcctgggcc tgcatcaggt gagccagtcg ctgatgagca gcctcacgcg gcacgggtgg | 2280 |
| caagactgcg tgatccccttt cctgcccctg gagagctccc aggcccagct cagccgggac | 2340 |
| acgtgcagcc tgctcagcag cctggtgtgg ctggacgagc actcccgggt cttcgccagg | 2400 |
| agggtggtca acacgttcaa ggcgcagcag ctgcgagccc gcaaggccca gtggaagaag | 2460 |
| gaacaggaca tccgggccct gcagcagcag cgccagcacc tggagggtga gcggcagcag | 2520 |
| gtggcctcgc tgagcgccgc ctactccgcc tacctccaga gctgctcgtc gtggcaggcg | 2580 |
| cagatggagg cgctccgggc ggccttcggg agccacatgc catttggggc tcaggggccc | 2640 |
| tacggggggcc cggggcctct gggggccccc ccgcccctcc cctcctggtt gggccaccag | 2700 |
| cctcccgccg cgccgccgtg gctggccggc tcgcccgcgc ccgccttccc gcccgcgccc | 2760 |
| gccttcccgc agccccccgc cttctcgccg ccccccgcgc ccccgcagag cccggggctg | 2820 |
| cagcccctca tcatccacca cgcgcagatg gtgcagctgg gcgtcaacaa ccacatgtgg | 2880 |
| aaccagcgag ggacccaggc gcccgaggac gagacgcaag gagcagagtg a | 2931 |

<210> SEQ ID NO 30
<211> LENGTH: 2370
<212> TYPE: DNA
<213> ORGANISM: Canis familiaris

<400> SEQUENCE: 30

| | | |
|---|---|---|
| atgaaaacta atcctagcat cttccaattt gccatcatct tcatattaat acttgagatc | 60 |
| agaatacaat tgtctgaaga aagtgatttt ctagttaaca gatcaaaagc aggtctcttt | 120 |
| cacattccca aagacctatc cctgaaaaca acaatcttag atatatcaca aaactatata | 180 |
| tctgagcttc agacttctga catcctatca ctatcaaagc tgaggatttt gattgtttct | 240 |
| tataatagaa ttcaatatct tgatatcagt gttttcaaat tcaaccagga attggaatac | 300 |
| ttggatctgt cccacaatga gttggggagg atttcttgcc atcctaccgt gaacctcaag | 360 |
| cacttagacc tttcatttaa tgcatttgat gatctaccca tatgcaaaga gtttggcaac | 420 |
| atgtctcaac tagagtttct ggggttgagt gccacacagt tacagaaatc tagcatgcta | 480 |
| ccaattgctt ctttgcatat cagaaaggtt ttactggtct taggagacac ttatgggaaa | 540 |
| aaagaagacc ctgagagcct tcaaaagctt aacacagaaa gtcttcacat tgttttccct | 600 |
| ataagaaagg aattcagttt tactctggat gtatcagtca gcactgcagt aagtctcgaa | 660 |
| ttgtctaata tcaaatgtgt gccagatggt catggatggt cttatttcca aaatgttctg | 720 |
| tcaaaacttc aaaagaattc aaggttatca agtcttactt taaacaacat tgaaacaact | 780 |
| tggaatttttt tcattatgct ccttcagttg gtttggcata caagcataga gtatttctca | 840 |
| atttcaaatg taaaactaca aggttaccct gacttcagag attttgatta ttctgacact | 900 |
| tcactgaagg ccttatctat acaccaagtc gttagtaatg cattcaattt gccacaaagt | 960 |
| tatatctata aaatcttttc aaatatgaac atccaaaatt tcacagtgtc tggtacgcac | 1020 |
| atggtccaca tggtttgccc atctcaaatt agtccatttc tgcatttgga tttttctaat | 1080 |
| aatctcttaa cagacattgt tttttaaaaat tgtagaaact tgattaaact ggagacactt | 1140 |
| agtttacaaa tgaatcaatt aaaagaactt gcaagtatag ctcaaatgac caacgagatg | 1200 |
| aagtctctac aacaattgga tattagccag aattctctaa ggtatgatga aaatgaagga | 1260 |

```
aactgctctt ggactagaag tttattaagt ttaaatatgt cttcaaatat acttactgac   1320
tctgttttca gatgtttacc tcccaaggtc aaggtgcttg atcttcacga taacagaata   1380
aggagcattc ctaaaccaat catgaagcta gaagatttgc aagaactcaa tgttgcttcc   1440
aattctttag cccactttcc tgactgtggt acttttaata ggctttctgt actgatcatt   1500
gactctaatt caatttccaa tccatcagct gatttcctcc agagctgcca taacattagg   1560
tccataagcg cagggaataa tccattccag tgtacatgtg agctgagaga atttgtccaa   1620
agtctaggcc aggtagcaag caaagtagta gagggttggc ctgattctta taagtgtgac   1680
tctccagaaa actataaggg aaccctactg aaggactttc acgtgtctcc gttatcctgc   1740
aacacaactc tgctgcttgt caccattggg gtcgctgtgc tagtgttcac tgttactgtg   1800
actgcgctct gtatctactt tgatctgccc tggtatctta ggatggtgtt tcagtggacc   1860
cagacccggc gcagggcaag aaacacaccc ttagaaaatc tccaaagaac catccagttc   1920
catgctttta tttcatatag cgggcatgat tctgcctggg tgaagagtga attactacca   1980
aacctagaaa agaagaaact aaggatttgt ctccatgaga gaaactttat tcctggcaag   2040
agcattgtgg aaaatatcat aaactgcatt gagaaaagtt acaagtccat ctttgttctg   2100
tctcccaact ttgttcagag tgagtggtgc cattatgaac tgtactttgc ccaccacaat   2160
ctctttcatg aaggatctaa taacttaatc ttgatcttgc tggaacctat tccacagtat   2220
tccattccta gcagctatca caagctcaaa aatctcatgg cacaaaggac ttatttggaa   2280
tggcccaagg agaagagcaa acatggactt ttttgggcta acctaagagc gtctattaat   2340
attaaattga gggagcaagc aaaaaaatag                                    2370
```

<210> SEQ ID NO 31
<211> LENGTH: 1155
<212> TYPE: DNA
<213> ORGANISM: Canis familiaris

<400> SEQUENCE: 31

```
gcgaagacgg cgctgcggtc cccggcgtcc ggccatggcc gccgagggct cccgcgcggg   60
gtccgcctcc ccggtctgcc ccaaggcttc cctgccctg gctgctctca acgtgcgagt    120
gcgccgccgc ctgtctctgt tcctgaacgt gcgcacgcag gtggcggccg actggaccgc   180
gctggccgag gagatgggct tcgagtacct ggagatccgg cacctggaga tgcacgccga   240
ccccacgggc aagctgctgg acgactggca gggacgccct ggcgcctcgg tgggccgcct   300
gcttgagctg ctcaccaagc tgggccgaga cgacgtgttg gtggaactgg ggcccagcat   360
cgaggaggat tgccaaaagt atattctgaa acagcagcag gaggagtctg agaagccctt   420
acaggtgcct gctgttgaca gcagtgaccc acggacacca gagcgagggg gcatcaccat   480
gcttgatgat ccctcagggc aaatgcctga gcgttttgat gccttcatct gctactgccc   540
cagcgatatc cagtttgttc aggaaatgat ccggcagctg aacagacaa actatcggct   600 gaagttgtgt gtgtctgatc gtgatgtctt gcctggcacc tgtgtctggt ccattgccag   660
cgagctcatt gagaagaggt gccgccggat ggtagtggtt gtctctgatg attacctgca   720
aagcagggaa tgtgacttcc agactaagtt tgcactcagt ctctctccag gtgcccatca   780
gaagcgactg atccccatca agtacaaggc aatgaagaaa gagttcccca gcatcctgcg   840
gttcatcact gtctgtgact acaccaaccc ctgcaccaag tcctggttct ggactcgcct   900
cgccaaggcc ctgtccctgc cctgaagact gccctgggac cgtgggtggg tgtgtgtcta   960
```

-continued

```
tctctcagcc tctgcgtgca cttctgcccc tgcttcctcc tgcagtggtt ggggtaagct    1020
gtgctccact tgcctcttca ttcctggaga tgccaactct gcagacatct gtagccactg    1080
tacctagctg ggacatggca tgtcatgtcc tttgtggaac cagtagctat taagtggcat    1140
gtccacatgc taggt                                                     1155
```

PATTERN RECOGNITION RECEPTOR EXPRESSION AS A MEASURE OF SYSTEMIC HEALTH

The instant application contains a Sequence Listing which has been submitted via EFS Web and is hereby incorporated by reference in its entirety. Said ASCII copy, created on Dec. 19, 2012, is named 9897-00-WO-HL_Sequence_Listing_ST25US.txt and is 49000 bytes in size.

BACKGROUND OF THE INVENTION

Humans and non-human mammals, including companion animals are susceptible to periodontal disease and other afflictions and conditions of the oral cavity. Periodontal disease develops, in part, as a consequence of the adherence of plaque, a mixture of oral bacteria and saliva components, to the surface of the teeth. This adherent plaque hardens to form tartar (calculus), which can lead to inflammation, swelling, and infection of the gums. There have been suggestions in the art that there might, in some instances, be a correlation between such diseases of the teeth and gums and other systemic diseases, including cardiac conditions. In a similar vein, there has also been speculation in the art that maintaining the teeth and gums of an animal might decrease the rate of mortality and extend the life span of that animal.

However, there do not appear to be any studies in the art that actually demonstrate the relationship of (a) oral health, (b) pattern recognition receptor expression levels, and (c) the beneficial effect of therapy of oral health conditions on systemic disease outcomes.

Accordingly, there is a need for studies that would establish whether or not there is a causal link between oral health conditions and the overall systemic health of the animal. In addition, if that causal link were to be established, then there would develop a need for a rapid, facile, accurate, and sensitive method for evaluating systemic health in subjects, particularly in companion animals, afflicted with an oral health condition.

BRIEF SUMMARY OF THE INVENTION

The present invention is directed to a method for measuring systemic health in a subject in need thereof, where the subject is afflicted with an oral health condition. The method comprises determining the expression level of at least one pattern recognition receptor in the subject, and then comparing that level of expression to a control. In one aspect of the invention, the control is a baseline control corresponding to the measured baseline level of expression of that same pattern recognition receptor (or those same pattern recognition receptors) in the afflicted animal before therapy. A healthy control level would be the level of expression in the same animal when the oral cavity is brought to a state of good oral health through intervention (complete dental prophylaxis) or good oral hygiene. In other aspects, the healthy control can be the measured level of expression of that same pattern recognition receptor (or those same pattern recognition receptors) in healthy control animals that are not afflicted with the oral health condition. According to the method, poor systemic health in an animal with an oral care condition, as it relates to the effect of oral health on systemic health, is indicated where the pattern recognition receptor expression levels measured in the tested subject are greater than those of the healthy control.

In certain embodiments, of this method, the pattern recognition receptor is selected from the group consisting of Toll Like Receptor 1 (TLR1), Toll Like Receptor 3 (TLR3), Toll Like Receptor 4 (TLR4), Toll Like Receptor 7 (TLR7), Toll Like Receptor 9 (TLR9), Toll Like Receptor 10 (TLR10), myeloid differentiation primary response gene 88 (MyD88), and Nucleotide Binding oligomerization domain containing protein 1 (NOD1).

In another embodiment, the method of the invention comprising determining an expression level of at least one second pattern recognition receptor in the subject afflicted with an oral health condition, comparing that level of expression to a control. Again, the baseline control level of expression can be that of the same afflicted animal (the expression level before treatment of the oral health condition), while the healthy control can be the level of expression determined for the same second pattern recognition receptor in healthy control animals not afflicted with the oral health condition. Good systemic health, i.e., as it relates to the effect of oral health on systemic health, is indicated where the expression level of the pattern recognition receptor measured in the tested subject is equal to or less than that of the healthy control, and poor systemic health (as it relates to the effect of oral health) is indicated where the expression level of the second pattern recognition receptor measured in the tested subject is greater than that of the healthy control. In particular aspects of this embodiment, the at least one second pattern recognition receptor is selected from the group consisting of Toll Like Receptor 1 (TLR1), Toll Like Receptor 3 (TLR3), Toll Like Receptor 4 (TLR4), Toll Like Receptor 7 (TLR7), Toll Like Receptor 9 (TLR9), Toll Like Receptor 10 (TLR10), myeloid differentiation primary response gene 88 (MyD88), and Nucleotide Binding oligomerization domain containing protein 1 (NOD1).

In certain embodiments, wherein the subject is a companion animal, and in particular aspects of this embodiment, the companion animal is a feline or the companion animal is a canine.

In certain embodiments of the methods of the invention, the oral care condition of the subject to be treated comprises periodontal disease. In particular aspects of these embodiments, the periodontal disease may comprise one or more of gingivitis, periodontitis, dental plaque, dental tartar, resorptive tooth lesion, mobile tooth, attachment loss, and gingival recession.

The present invention is further directed to a method for determining the efficacy of treatment of an oral health condition in an animal in need thereof and/or for monitoring the efficacy of a treatment on the systemic health of an animal in need thereof, where that animal is afflicted with an oral health condition, and wherein the treatment comprises treatment or therapy of the oral health condition. This method comprises (a) determining the expression level of a first pattern recognition receptor in the animal at a first time point prior to or shortly after the treatment, (b) determining the expression level of the same pattern recognition receptor in the animal at a second time point subsequent to the first time point, and (c) comparing the expression levels measured at the two time points. According to this method, efficacy of the treatments is indicated where the expression level at the later time point is lower than that measured at the first time point. In another aspect of this method the level of expression of two or more pattern recognition receptors may be measured and compared at each time point. In certain aspects of these embodiments, the first time point may be a month, three weeks, two weeks, one week or less prior to the treatment. In other aspects of these embodiments, the first time point is taken less than a day before the treatment. In still another aspect, the first time point is taken less than a day after the treatment.

The present invention is also directed to a method for diagnosing a systemic health condition in a subject in need thereof, where the subject is an animal afflicted with an oral care condition. This method comprises determining the expression level of a first pattern recognition receptor in the subject comparing it to a control value. In one aspect of the invention, the control is a baseline control corresponding to the measured baseline level of expression of that same pattern recognition receptor (or those same pattern recognition receptors) in the afflicted animal before therapy. In another aspect, the control value is a healthy control level corresponding to the level of expression in the same animal after the oral cavity is brought to a state of good oral health through intervention (complete dental prophylaxis) or good oral hygiene. In another aspect, the healthy control can be measured as the level of expression of that same pattern recognition receptor (or those same pattern recognition receptors) in healthy control animals that are not afflicted with the oral health condition. According to the method, poor systemic health in an animal with an oral care condition, as it relates to the effect of oral health on systemic health, is indicated where the pattern recognition receptor expression levels measured in the tested subject are greater than those of the healthy controls.

The present invention is also directed to a method for treating a chronic systemic inflammation in an animal in need thereof and afflicted with an oral health condition. The method comprises subjecting the animal to a dental prophylaxis treatment designed to ameliorate periodontal disease in the subject animal in need thereof.

In a particular aspect of the present invention, the pattern recognition receptor or receptors, the expression levels of which are measured in the above-described methods of the invention, are selected from the group consisting of Toll Like Receptor 1 (TLR1), Toll Like Receptor 3 (TLR3), Toll Like Receptor 4 (TLR4), Toll Like Receptor 7 (TLR7), Toll Like Receptor 9 (TLR9), Toll Like Receptor 10 (TLR10), myeloid differentiation primary response gene 88 (MyD88), and Nucleotide Binding oligomerization domain containing protein 1 (NOD 1), and the oral health condition of the indicated subjects and animals indicates the presence of periodontal disease.

In addition, in particular aspects of these embodiments, the subject or animal afflicted with and oral health condition is a companion animal, e.g., canine or feline companion animal, such as a dog or a cat.

The present invention also encompasses kits useful for practice of the methods described herein. In one embodiment, the present invention includes a kit for determining the expression level of a feline pattern recognition receptor, where that kit comprises forward and reverse primers suitable for polymerase chain reaction amplification of cDNA corresponding to at least one pattern recognition receptor selected from the group consisting of feline Toll Like Receptor 1 (TLR1), feline Toll Like Receptor 3 (TLR3), feline Toll Like Receptor 4 (TLR4), feline Toll Like Receptor 7 (TLR7), feline Toll Like Receptor 9 (TLR9), feline Toll Like Receptor 10 (TLR10), feline myeloid differentiation primary response gene 88 (MyD88), and feline Nucleotide Binding oligomerization domain containing protein 1 (NOD1).

In another embodiment, the present invention includes a kit for determining the expression level of a canine pattern recognition receptor, where that kit comprises forward and reverse primers suitable for polymerase chain reaction amplification of cDNA corresponding to at least one pattern recognition receptor selected from the group consisting of canine Toll Like Receptor 1 (TLR1), canine Toll Like Receptor 3 (TLR3), canine Toll Like Receptor 4 (TLR4), canine Toll Like Receptor 7 (TLR7), canine Toll Like Receptor 9 (TLR9), feline Toll Like Receptor 10 (TLR10), canine myeloid differentiation primary response gene 88 (MyD88), and canine Nucleotide Binding oligomerization domain containing protein 1 (NOD1).

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

As demonstrated herein, the present inventors have discovered that there is a systemic response to poor oral health and there is a causal connection between oral health and systemic health. The presently-described invention, which is based in part on this discovery, encompasses measuring systemic health in a subject in need thereof, where the subject is afflicted with an oral health condition. The methods described herein comprise determining the expression level of at least one pattern recognition receptor in the subject, and then comparing that level expression to a control, where increases in the expression levels of pattern recognition receptors is indicative of poor or declining systemic health in the subject afflicted with an oral health condition.

Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication, which might be used in connection with the invention.

As used herein and in the appended claims, the singular forms "a", "an", and "the" include plural reference unless the context clearly dictates otherwise.

As used herein, the term "animal" is a human, a non-human animal, or a non-human mammal, where the term non-human animal includes non-human primates (e.g., monkeys, chimpanzees, apes etc.), companion animals and house pets (e.g., dogs, cats, rabbits etc.), laboratory animals, domesticated animals, livestock and farm animals (e.g., horses, goats, sheep, swine, llamas, alpacas, bovine animals etc.). In one embodiment, the animal is a non-primate mammal. In another embodiment, the animal is a non-human primate. In a specific embodiment, the animal is a domesticated companion animal or "house" pet, such as canine or a feline. In one aspect, the animal is a dog. In another aspect the animal is a cat.

As used herein, "oral care condition" is any disorder or condition of the oral cavity, including disorders or conditions of the teeth, oral mucosa, gingiva and tongue. Such conditions include periodontal disease, which may encompass, without limitation, one or more of gingivitis, periodontitis, dental plaque, dental tartar, resorptive tooth lesion, gingival recession, gingival attachment loss, mobile tooth, and combinations thereof.

According to the invention, the phrase "animal in need thereof," refers to a human or a non-human animal for whom or for which treatment is required for an oral care condition including, but not limited to, periodontal disease, which may encompass, without limitation, one or more of gingivitis, periodontitis, dental plaque, dental tartar, resorptive tooth lesion, gingival recession, gingival attachment loss, mobile tooth, and combinations thereof.

The term "treating," as used herein, means to cure, inhibit, ameliorate, or arrest the development, relieve the symptoms or effects of, or to ameliorate, or cause the reduction in the symptoms or effects of an oral care condition in an animal in need of treatment for that condition. Accordingly, it should be recognized that the terms "ameliorating," "treating," and "controlling," are not intended to limit the scope of the invention and that, although distinguishable from one another, there can be overlap amongst these terms.

The term "companion animal" used in the present invention includes any non-human animal suitable for being kept as a pet by humans including a dog, a cat, and a rodent. All aspects of the present invention are preferably for the treatment of dogs and/or cats.

The term "dog" includes those dogs which are companion animals such as *Canis familiaris*, working dogs and the like. The term dog is synonymous with the term canine.

The term "cat" includes those cats which are companion animals known as domestic cats or house cats, or *Felis domesticus*. The term cat is synonymous with the term feline.

The phrase "pattern recognition receptor," as used herein is intended to encompass not only Toll Like Receptors and other receptors and receptor classes classified as pattern recognition receptors, but also the proteins of the related signaling pathways that function with and coordinately expressed along with the pattern recognition receptors including, without limitation, MYD88, NOD-1, NOD-2, TIRAP, TIR, TRIF, TRAM, TAK1, TRAF3, TBK1, NEMO, IRAK, IKKi, and TRAF6, and the like as described in, for example, Kawai et al., "The Roles of TLRs, RLRs and NLRs in Pathogen Recognition" *International Immunology* (2009) 21 (4): 317-337, and Mahanonda et al., "Toll-Like Receptors and Their Role in Periodontal Health and Disease," *Periodontol* 2000 (2007) 43: 41-55, both of which are hereby incorporated by reference in their entirety.

Methods of the Invention

In one embodiment, the present invention is directed to a method for measuring systemic health in a subject in need thereof, where the subject is afflicted with an oral health condition. This method comprises determining a subject first expression level of a first pattern recognition receptor in the subject and comparing that subject first expression level to a control first expression level of the first pattern recognition receptor. In one aspect of the invention, the healthy control expression level of the first patter recognition receptor is determined in healthy animals that are not afflicted with the oral health condition, i.e., as demonstrated below in the Examples. In another aspect, the healthy control level would be the level of expression in the same animal when the oral cavity is brought to a state of good oral health through intervention (complete dental prophylaxis) or good oral hygiene. Based upon this analysis, it can be concluded that good systemic health in an animal afflicted with an oral health condition is indicated where the value of the first expression level is equal to or less than that of the control. Similarly, were the subject first expression level is greater than that of the healthy control, it can be concluded that the tested animal exhibits poor systemic health, as it relates to the oral health condition.

In another aspect of these embodiments of the invention, the control level of expression of the pattern recognition receptor is the baseline control, measured in the afflicted animal prior to or shortly after treatment of the oral health condition. In this instance increased levels of expression of the pattern recognition receptor (i.e., greater than the baseline control value) is diagnostic of the existence or development of a systemic health condition, while decreased levels of expression of the pattern recognition receptor (i.e., less than the baseline control value) is diagnostic of the amelioration of a systemic health condition in the animal afflicted with an oral health condition.

In certain aspects of these embodiments, the expression level of the pattern recognition receptor can be measured for a pattern recognition receptor selected from the group consisting of Toll Like Receptor 1 (TLR1), Toll Like Receptor 3 (TLR3), Toll Like Receptor 4 (TLR4), Toll Like Receptor 7 (TLR7), Toll Like Receptor 9 (TLR9), Toll Like Receptor 10 (TLR10), myeloid differentiation primary response gene 88 (MYD88), and Nucleotide Binding oligomerization domain containing protein 1 (NOD1).

Another aspect of this embodiment comprises determination of the expression level of at least one second pattern recognition receptor in the subject comparing the subject second expression level to a control second expression level of the second pattern recognition receptor. Again, in one aspect, the control expression levels can be determined in healthy animals not afflicted with the oral health condition. Here, good systemic health in the animal afflicted with the oral health condition is indicated where the value of the second expression level is equal to or less than that of the control, while poor systemic health is indicated in the animal afflicted with the oral health condition where the value of the second expression level is greater than that of the control. The second expression level of the pattern recognition receptor can be measured for a pattern recognition receptor selected from, but not limited to, the group consisting of TLR1, TLR3, TLR4, TLR7, TLR9, TLR10, MYD88, and NOD1. In still another aspect the control level of expression of the second pattern recognition receptor is the baseline control, measured in the afflicted animal prior to or shortly after treatment of the oral health condition. In this instance increased levels of expression of the pattern recognition receptor (i.e., greater than the baseline control value) is diagnostic of the existence, development, and/or progression of a systemic health condition, while decreased levels of expression of the second pattern recognition receptor (i.e., lower than the baseline control value) is diagnostic of the amelioration of a systemic health condition in the animal afflicted with an oral health condition.

In the method described herein the subject or animal tested may be a companion animal. In particular aspects of these embodiments, the companion animal is a feline, while in other aspects, the companion animal is a canine.

In certain embodiments of the methods described herein, expression levels of the pattern recognition receptors are determined by measuring the levels of mRNA encoding the pattern recognition receptor of interest. In one aspect of this embodiment, the mRNA is first converted to cDNA and then measured by quantitative, real time polymerase chain reactions (qRT-PCR), as described in more detail in the Examples. In certain aspects of the present invention, the qRT-PCR data are "normalized" against a "calibrator mRNA."

In one embodiment, the animal to be treated is afflicted with an oral care condition comprising periodontal disease, which may include, without limitation, one or more of gingivitis, periodontitis, dental plaque, dental tartar, resorptive tooth lesion, mobile tooth, attachment loss, and gingival recession.

In another embodiment, the present invention is directed to a method for monitoring the efficacy of a treatment on the systemic health of an animal in need thereof, wherein the animal is afflicted with an oral health condition and wherein the treatment comprises therapy of the oral health condition. This method comprises determining a first expression level of a first pattern recognition receptor in the animal at a first time point, wherein the first time point prior to or shortly after the treatment, followed by determining a second expression level of the first pattern recognition receptor in the animal at a second time point subsequent to the first time point. The values determined for expression level of the pattern recognition receptor are compared and efficacy of the treatment is indicated where first expression level is greater than the second expression level. Again, these expression levels can be determined for one or more than one of a pattern recognition receptor selected from but not limited to the group consisting of TLR1, TLR3, TLR4, TLR7, TLR9, TLR10, MYD88, and NOD1.

In certain embodiments, this method for monitoring efficacy of a treatment may be used where the subject or animal tested is be a companion animal. In particular aspects of these embodiments, the companion animal is a feline, while in other aspects, the companion animal is a canine. In other aspects of this embodiment, the expression levels of the pattern recognition receptor(s) are determined using quantitative real time, polymerase chain reaction analysis (qRT-PCR) of mRNA.

The present invention, in a further embodiment, is also directed to a method of determining efficacy of treatment of an oral health condition in an animal in need thereof. This method comprises determining a first expression level of a first pattern recognition receptor in the animal at a first time point. This step is followed by determining a second expression level of the first pattern recognition receptor in the animal at a second time point subsequent to the first time point. The pattern recognition receptor expression levels determined at the two time points are compared and efficacy of the treatment is indicated by the first expression level being greater than the second expression level.

In a still further embodiment, the present invention is directed to a method for diagnosing a systemic health condition in a subject in need thereof, wherein the subject is afflicted with an oral health condition. This method comprises determining a subject first expression level of a first pattern recognition receptor in the subject, and then comparing that expression level to a control first expression level of the first pattern recognition receptor. Again the control value is determined in healthy control animals not afflicted with the oral health condition. Existence of a systemic health condition is indicated by the subject first expression level being greater than the control first expression level and absence of a systemic health condition is indicated by the subject first expression level being less than or equal to the control first expression level. Moreover, in one aspect of this embodiment, severity of the health condition is indicated by the absolute value of a ratio of the subject first expression level to the control first expression level. In another aspect of this embodiment, the control value can be that determined for the subject animal, per se, at a point in time when the animal was healthy and was not afflicted with either an oral health condition or a systemic health condition.

In certain aspects of these embodiments, the expression levels can be determined for one or more than one of a pattern recognition receptor selected from, but not limited to, the group consisting of TLR1, TLR3, TLR4, TLR7, TLR9, TLR10, MYD88, and NOD1.

In other aspects of this embodiment, the subject is a companion animal, e.g., a feline or a canine.

The oral health condition afflicting the subjects and animals for which the described methods are carried out, comprise at least one of periodontal disease, including, e.g., one or more of gingivitis and periodontitis, dental plaque, dental tartar, gingival recession, gingival attachment loss, and mobile tooth.

The present invention is also directed to a method for treating a chronic systemic inflammation in an animal in need thereof and afflicted with an oral health condition. The method comprises subjecting the animal to a dental prophylaxis treatment designed to ameliorate one or more oral health conditions, which may comprise periodontal disease, which may include gingivitis and periodontitis, dental plaque, dental tartar, gingival recession, gingival attachment loss, mobile tooth, and combinations of two or more thereof.

In certain embodiments, the animal tested or treated according to the methods described herein is an animal afflicted with an oral care condition and in need of such testing. In certain embodiments, that animal is a non-human animal, or a non-human mammal, e.g., a non-human primate (e.g., monkeys, chimpanzees, apes etc.), a companion animal, or a house pet (e.g., dog, cat, rabbit etc.), a laboratory animal, a domesticated animal (including livestock and farm animals such as but not limited to horses, goats, sheep, swine, llamas, alpacas, bovine animals etc.). In one embodiment, the animal is a domesticated companion animal or "house" pet, such as canine or a feline. In one aspect, the animal is a dog. In another aspect the animal is a cat.

Kits of the Invention

The present invention is further directed to kits useful in the practice of the methods described herein, i.e., useful for determining the expression level of one or more feline pattern recognition receptors. In one embodiment, the kit comprises forward and reverse primers suitable for polymerase chain reaction amplification of cDNA corresponding to at least one pattern recognition receptor selected from, but not limited to, the group consisting of feline Toll Like Receptor 1 (TLR1), feline Toll Like Receptor 3 (TLR3), feline Toll Like Receptor 4 (TLR4), feline Toll Like Receptor 7 (TLR7), feline Toll Like Receptor 9 (TLR9), feline Toll Like Receptor 10 (TLR10), feline myeloid differentiation primary response gene 88 (MyD88), and feline Nucleotide Binding oligomerization domain containing protein 1 (NOD1).

In another embodiment, a kit of the invention is useful for determination of the expression level of one or more canine pattern recognition receptors. In one aspect of this embodiment, the kit comprises forward and reverse primers suitable for polymerase chain reaction amplification of cDNA corresponding to at least one pattern recognition receptor selected from the group consisting of, but not limited to, canine Toll Like Receptor 1 (TLR1), canine Toll Like Receptor 3 (TLR3), canine Toll Like Receptor 4 (TLR4), canine Toll Like Receptor 7 (TLR7), canine Toll Like Receptor 9 (TLR9), feline Toll Like Receptor 10 (TLR10), canine myeloid differentiation primary response gene 88 (MyD88), and canine Nucleotide Binding oligomerization domain containing protein 1 (NOD1).

In particular aspects of these embodiments, the kits can contain one or more of primers or pairs of primers useful for PCR analysis, as set forth in the Examples, below, (e.g., SEQ ID NO. 1-SEQ ID NO. 16) or those readily designed, e.g., using commercially-available software based on sequences corresponding to the gene expression level to be analyzed (e.g., SEQ ID NO. 17-SEQ ID NO. 31).

Examples

The studies described herein were conducted with cats and document the effect of periodontal disease on systemic pattern recognition receptor expression, demonstrating a causal connection between oral and systemic health. In the pilot study describe below, pattern recognition receptors (TLR1, TLR3, TLR4, TLR7, TLR9, TLR10, MYD88, and NOD1) were shown to be differentially expressed in cats with good oral health as compared to cats with poor oral health. In a first intervention study, it was shown that cats with poor oral health have up-regulated systemic pattern recognition receptor expression levels compared to those same cats with healthy mouths, and that a complete dental prophylaxis attenuates systemic expression of these mediators of host immune response. These results were reproduced in a second intervention study in which the cats with severe periodontal disease were brought to a state of good oral health with a concomitant, statistically significant, reduction in the systemic expression levels of three pattern recognition receptors. In addition, it was noted that there was a clear numerical decrease in expression levels of all the pattern recognition receptor levels as a function of oral health intervention that was seen for only one pattern recognition receptor (TLR10) in control animals. Taken together, the data presented herein provide strong evidence supporting systemic response to poor oral health, thereby establishing a causal connection between oral and systemic health.

Published reviews describing the roles played by pattern recognition receptors, the related signaling pathways and proteins thereof, and biochemical consequences of pattern receptor recognition ligand binding are provided, inter alia, in Kawai et al., "The Roles of TLRs, RLRs and NLRs in Pathogen Recognition" *International Immunology* (2009) 21 (4): 317-337 and Mahanonda et al., "Toll-Like Receptors and Their Role in Periodontal Health and Disease," *Periodontol* 2000 (2007) 43: 41-55, both of which are hereby incorporated by reference in their entirety.

Materials and Methods

Sample Collection: Samples of feline whole blood were collected into PAXgene blood RNA tubes (Qiagen, Valencia, CA) and frozen until analysis. These blood samples were used to assess expression levels of the pattern recognition receptors (TLR1, TLR3, TLR4, TLR7, TLR9, TLR10, MYD88, and NOD1).

cDNA Synthesis: cDNA was prepared from the collected mRNA using the Ovation™ System (NuGen Technologies, San Carlos, CAP) according to the manufacturer's instructions.

Primers, Annealing Temperatures, and Thermal Cycler Programming: For primer annealing and first strand synthesis, the following program was used: samples were maintained at 65° C. for 5 minutes followed by a return to 4° C. and holding at that temperature until subsequent steps were to be performed. Amplification primers used included those of SEQ ID NO:1 (forward primer for analysis of feline TLR 9); SEQ ID NO:2 (reverse primer for analysis of feline TLR 9); SEQ ID NO:3 (forward primer for analysis of feline TLR 10); SEQ ID NO:4 (reverse primer for analysis of feline TLR 10); SEQ ID NO:5 (forward primer for analysis of feline NOD1); SEQ ID NO:6 (reverse primer for analysis of feline NOD1); SEQ ID NO:7 (forward primer for analysis of feline MYD88); SEQ ID NO:8 (reverse primer for analysis of feline MYD88); SEQ ID NO:9 (forward primer for analysis of feline TLR 1); SEQ ID NO:10 (reverse primer for analysis of feline TLR 1); SEQ ID NO:11 (forward primer for analysis of feline TLR 3); SEQ ID NO:12 (reverse primer for analysis of feline TLR 3); SEQ ID NO:13 (forward primer for analysis of feline TLR 4); SEQ ID NO:14 (reverse primer for analysis of feline TLR 4); SEQ ID NO:15 (forward primer for analysis of feline TLR 7);and SEQ ID NO:16 (reverse primer for analysis of feline TLR 7).

The relevant nucleotide sequences for feline TLR 9, TLR 10, NOD1, MYD88, TLR1, TLR3, TLR 4 and TLR 7 are provided in SEQ ID NO:17 to SEQ ID NO: 24, respectively. The relevant nucleotide sequences for canine TLR9, TLR2, TLR4, TLR7, CAM1, TLR1, and MYD88 are provided in SEQ ID NO: 25 TO SEQ ID NO: 31, respectively.

After annealing, first strand synthesis was carried out by incubation at 48° C. for 60 minutes, incubation at 70° C. for 15 minutes, followed by a return to 4° C. and holding at that temperature until subsequent steps were to be performed.

Second strand synthesis was carried out, incubating the samples at 37° C. for 30 minutes, and then 75° C. for 15 minutes, followed by a return to 4° C. and holding at that temperature until subsequent steps were to be performed.

SPIA® Amplification (NuGEN Technologies, San Carlos, Calif.): Amplification was carried out at 48° C. for 30 minutes, followed by a hold at 4° C., and then at 48° C. for 30 minutes, and 95° C. for 5 minutes, followed by a hold at 4° C.

Quantitative, real time polymerase chain reaction (qRT-PCR), was carried out using an Applied Biosystems (Torrance CA) 7500 Fast Real-Time PCR System and 7500 Software 2.0.1.

Gene Expression Calculations: The Comparative Ct method (AACt-method): The comparative Ct method is a mathematical model that calculates changes in expression of the gene of interest after the dental treatment, relative to that of a calibrator. Prior to experimental sample analysis, a validation experiment was run to ensure that the amplification efficiencies of the gene of interest and the reference gene or "housekeeping" gene are equal. The validation experiment consisted of a dilution series of cDNA containing the genes of interest (pattern recognition receptors) and the reference gene (18S). The slopes of a semi-log regression analysis of the dilution series (ACt vs. log input amount) should be approximately equal for a valid AACT calculation (±0.1). Assessing the relative efficiencies of the target gene of interest amplification and the reference endogenous control amplification was achieved by running serial dilutions using one pooled sample. The CT values generated from each dilution point (target vs. reference) were used in the OCT calculation (ΔCT=CT target−CT reference). All of the genes of interest passed this validation test.

Statistical Analysis and Methods: Fold Change. Data Assist™ v. 3.0 Software (Applied Biosystems) was used for data analysis which uses the comparative CT method for calculating relative quantification of gene expression. It contains a filtering procedure for removal of outliers, various normalization methods based on single or multiple genes, and provides relative quantification analysis of gene expression through a combination of statistical analysis and interactive visualization. A p-value cut off of 0.05 was used to select significant gene expression differences from the results obtained from the DataAssist software.

Example 1

Pilot Study

This experiment was intended to determine whether or not pattern recognition receptors (TLR1, TLR3, TLR4, TLR7, TLR9, TLR10, MYD88, and NOD1) were differentially expressed in cats with good oral health as compared to cats with poor oral health.

In this study age matched cats were selected from among those undergoing their annual dental prophylaxis and that were deemed to be in either good or poor oral health at the time of this procedure. Selection was done by examination of their oral health status that was recorded just prior to their dental cleaning Particular attention was paid to gingivitis status because a systemic response to poor oral health was hypothesized to be influenced by this metric. Two groups of cats were established, each with seventeen members; one with "poor" oral health and the other with relatively good oral health.

With respect to the "poor" oral health group, (1) all seventeen members were deemed to have "severe" gingivitis; (2) plaque was characterized as "medium" in sixteen members and "heavy" in one member, and (3) calculus was characterized as "light" in two members, "medium" in ten members, and "heavy" in five members.

With respect to the "good" oral health group, (1) all seventeen members were deemed to have "mild" gingivitis; (2) plaque was characterized as "light" in all seventeen members, and (3) calculus was characterized as "light" in fourteen members, and "medium" in three members.

Blood samples from these cats were collected into PAXgene blood RNA tubes and stored frozen until analysis. mRNA was isolated from these samples and RNA encoding the Pattern Recognition Receptor (PRR) mRNA for TLR1, TLR3, TLR4, TLR7, TLR9, TLR10, MYD88, and NOD1, was converted to double-stranded DNA and amplified by qRT-PCR, according to the methods described above.

Quantitative analysis of these blood samples showed that, numerically, all of the pattern recognition receptors were up-regulated in cats with periodontal disease, even though only the TLR10 expression differences were statistically different. NOD1 and TLR7 showed an elevated expression level in cats with periodontal disease relative to the set of cats with "good" oral health, with these differences trending toward statistical significance (0.05<p<0.10), as demonstrated in Table 1, below.

TABLE 1

| PRR Target | AVG Δ Ct Poor Oral Health Set | AVG Δ Ct Good Oral Health Set | ΔΔ Ct: Good/Poor Oral Health | Fold Change | P-Value |
| --- | --- | --- | --- | --- | --- |
| MYD88 | −2.81 | −2.44 | −0.37 | 1.29 | 0.55 |
| NOD1 | 4.38 | 5.58 | −1.19 | 2.29 | 0.06 |
| TLR1 | −6.96 | −6.11 | −0.85 | 1.80 | 0.13 |
| TLR10 | −1.20 | 0.43 | −1.62 | 3.08 | 0.03 |
| TLR 3 | 3.34 | 4.55 | −1.22 | 2.32 | 0.17 |
| TLR4 | −1.55 | −1.12 | −0.44 | 1.35 | 0.52 |
| TLR7 | 1.35 | 2.27 | −0.92 | 1.90 | 0.06 |
| TLR9 | 0.47 | 1.28 | −0.82 | 1.76 | 0.23 |

The data of Table 1 illuminate the pilot study differential pattern recognition receptor expression between the cats of the "poor" oral health group and that of the "good" oral health group of cats. The Fold Change is the difference between the cats of the "poor" oral health group and that of the "good" oral health group of cats. Statistically significant differences are identified as those with a P-value less than 0.05 and those data indicating a trend toward significance are those with a P-value greater than 0.05 but less than 0.1.

As demonstrated by the above data this study demonstrated that pattern recognition receptors (TLR1, TLR3, TLR4, TLR7, TLR9, TLR10, MYD88, and NOD1) were differentially expressed in cats with good oral health as compared to cats with poor oral health.

Example 2

First Intervention Study

This first intervention study was designed to determine whether or not the expression levels of the pattern recognition receptors (TLR1, TLR3, TLR4, TLR7, TLR9, TLR10, MYD88, and NOD1) would respond to oral care therapy, e.g., periodontal disease intervention, and thereby establish a causal link between oral health and systemic health.

Thirteen cats were selected from a laboratory feline colony that could be classified as having "poor" oral health, as determined by a gingivitis score classified as "severe" upon initial visual inspection. Prior to initiation of the study, multiple measures of oral health were documented for each cat. These measures included dental plaque, tartar, toot stain, and gingivitis using metrics from the Logan/Boyce dental substrate quantification method (Logan et al. (1994) "Oral health assessment in dogs: parameters and methods" J. Vet. Dent. 11 (2): 58-63), as well as the number of missing teeth, the number of mobile teeth, the number of teeth with gingival recession, the sum of the recession scores, the average recession score, the number of teeth with pockets greater than 1 mm, the average pocket depth greater than 1 mm, the number of teeth with furcations, the average furcation grade, the number of teeth with resorptive lesions, and then number of teeth with fractures.

The average gingivitis score for the group was 1.0±0.2 with values ranging from 0.6 to 1.3. Since the range of possible scores for gingivitis according to the method used is between 0.3 and 3, the average of 1.0 would be considered to be moderate inflammation. In contrast, plaque and calculus scores were high, with averages of 12.6 and 5.0, respectively. Possible plaque scores range from 0 to 24 and possible calculus scores range from 0 to 12 so the cats with the values stated were considered to have substantial substrate accumulation. The scoring standards for grading gingivitis, dental plaque, and calculus, are provided in Tables 2, 3, and 4, respectively.

Table 2 provides the criteria for grading gingivitis. Scored gingivae are divided vertically into mesial, buccal, and distal thirds, and each third receives a separate numerical score based on the degree of gingival inflammation using the scale below. For each tooth, the scores for each third are averaged to obtain a whole-tooth score, and the sum of the whole-tooth scores divided by the number of teeth scored is the final, whole-mouth gingival score.

TABLE 2

Gingivitis Scoring

| | |
|---|---|
| 0 | Normal Gingiva |
| 0.5 | Normal inflammation; slight redness |
| 1.0 | Moderate inflammation and redness; no bleeding on probing |
| 2.0 | Moderate inflammation with sever redness; bleeding on probing |
| 3.0 | Severe inflammation and redness, edema, ulceration, and spontaneous bleeding |

Table 3 provides the grading criteria for dental plaque. Plaque is disclosed with a 2% eosin solution. The facial surface of each elevated tooth is divided horizontally, and each half is assigned a separate numerical score based on percent plaque coverage and dye intensity found in the Table 3 below. For each half, coverage is multiplied by intensity, and the results are summed to obtain a whole-tooth plaque score. The sum of the whole-tooth plaque scores is divided by the number of teeth scored to obtain a whole-mouth plaque score.

TABLE 3

| Percent Coverage | Intensity |
|---|---|
| 0 No plaque detected | 1 Light (pink) |
| 1 Plaque coverage <25% | 2 Medium (red) |
| 2 Plaque coverage 25 to <50% | 3 Dark (deep red) |
| 3 Plaque coverage 50 to <75% | |
| 4 Plaque coverage 75 to <100% | |

Table 4 provides the criteria for grading calculus. The facial surface of each evaluated tooth is divided into vertical thirds, and each third is assigned a separate numerical score based on the percent coverage using the scale set forth in Table 4 below. Coverage scores for each tooth are added to obtain a whole-tooth calculus score, and the sum of the whole-tooth calculus scores divided by the number of teeth scored is the final whole-mouth calculus score.

TABLE 4

Percent Coverage

| | |
|---|---|
| 0 | No calculus detected |
| 1 | Calculus coverage <25% |
| 2 | Calculus coverage 25 to <50% |
| 3 | Calculus coverage 50 to <75% |
| 4 | Calculus coverage 75 to <100% |

Fasting blood samples were drawn just prior to and just after a complete dental prophylaxis performed according to standard procedure on day 1. Additional blood samples were taken on day 3, 8, and 15 after the complete dental prophylaxis. All blood samples were collected into PAXgene blood RNA tubes using standard procedures, and the samples were frozen until analysis. These blood samples were used to assess the expression levels of the PRRs (TLR1, TLR3, TLR4, TLR7, TLR9, TLR10, MYD88, and NOD1) by qRT-PCR, according to the method described above.

Quantification of the relative levels of expression of the pattern recognition receptors targeted in this study is presented in Table 5.

TABLE 5

| Target | Day | Median ΔCt | Median ΔΔCt | Median RQ | Median Fold Change | P-value | Mean ΔCt | Mean ΔΔCt | Mean RQ | Mean Fold Change |
|---|---|---|---|---|---|---|---|---|---|---|
| MYD88 | Pre | 13.80 | 0.00 | 1.000 | 1.000 | — | 14.08 | 0.00 | 1.00 | 1.00 |
| MYD88 | Post | 13.75 | −0.04 | 1.026 | 1.026 | 0.6419 | 13.74 | −0.34 | 1.27 | 1.27 |
| MYD88 | 3 | 12.68 | −1.12 | 2.172 | 2.172 | 0.1290 | 11.35 | −2.73 | 6.64 | 6.64 |
| MYD88 | 8 | 13.44 | −0.36 | 1.284 | 1.284 | 0.5695 | 13.67 | −0.41 | 1.33 | 1.33 |
| MYD88 | 15 | 15.67 | 1.87 | 0.274 | −3.655 | 0.1615 | 15.29 | 1.21 | 0.43 | −2.31 |
| NOD1 | Pre | 15.90 | 0.00 | 1.000 | 1.000 | — | 16.70 | 0.00 | 1.00 | 1.00 |
| NOD1 | Post | 16.07 | 0.17 | 0.886 | −1.128 | 0.4951 | 16.02 | −0.68 | 1.60 | 1.60 |
| NOD1 | 3 | 16.13 | 0.23 | 0.852 | −1.174 | 0.3222 | 14.87 | −1.83 | 3.56 | 3.56 |
| NOD1 | 8 | 16.96 | 1.06 | 0.480 | −2.082 | 0.9179 | 16.81 | 0.11 | 0.93 | −1.08 |
| NOD1 | 15 | 18.95 | 3.06 | 0.120 | −8.316 | 0.0429 | 18.83 | 2.12 | 0.23 | −4.36 |
| TLR1 | Pre | 6.54 | 0.00 | 1.000 | 1.000 | — | 6.60 | 0.00 | 1.00 | 1.00 |
| TLR1 | Post | 6.47 | −0.07 | 1.049 | 1.049 | 0.7705 | 6.38 | −0.22 | 1.16 | 1.16 |
| TLR1 | 3 | 6.46 | −0.08 | 1.057 | 1.057 | 0.4802 | 5.39 | −1.22 | 2.32 | 2.32 |
| TLR1 | 8 | 7.45 | 0.92 | 0.530 | −1.887 | 0.2237 | 7.52 | 0.91 | 0.53 | −1.89 |
| TLR1 | 15 | 8.98 | 2.45 | 0.183 | −5.459 | 0.0019 | 9.28 | 2.68 | 0.16 | −6.40 |
| TLR10 | Pre | 15.26 | 0.00 | 1.000 | 1.000 | — | 14.75 | 0.00 | 1.00 | 1.00 |
| TLR10 | Post | 13.50 | −1.76 | 3.380 | 3.380 | 0.1846 | 13.75 | −1.00 | 1.99 | 1.99 |
| TLR10 | 3 | 15.43 | 0.17 | 0.887 | −1.128 | 0.7306 | 14.10 | −0.65 | 1.56 | 1.56 |
| TLR10 | 8 | 14.67 | −0.59 | 1.506 | 1.506 | 0.4993 | 15.29 | 0.54 | 0.69 | −1.45 |
| TLR10 | 15 | 16.24 | 0.98 | 0.507 | −1.973 | 0.0202 | 16.83 | 2.08 | 0.24 | −4.22 |
| TLR4 | Pre | 13.50 | 0.00 | 1.000 | 1.000 | — | 13.56 | 0.00 | 1.00 | 1.00 |
| TLR4 | Post | 13.40 | −0.10 | 1.071 | 1.071 | 0.7047 | 13.27 | −0.29 | 1.23 | 1.23 |
| TLR4 | 3 | 12.48 | −1.02 | 2.021 | 2.021 | 0.1861 | 10.84 | −2.72 | 6.61 | 6.61 |
| TLR4 | 8 | 12.87 | −0.63 | 1.551 | 1.551 | 0.8882 | 13.46 | −0.10 | 1.07 | 1.07 |
| TLR4 | 15 | 14.93 | 1.43 | 0.370 | −2.700 | 0.0452 | 15.21 | 1.65 | 0.32 | −3.13 |
| TLR7 | Pre | 14.60 | 0.00 | 1.000 | 1.000 | — | 14.89 | 0.00 | 1.00 | 1.00 |
| TLR7 | Post | 15.34 | 0.74 | 0.597 | −1.676 | 0.5124 | 15.54 | 0.64 | 0.64 | −1.56 |

TABLE 5-continued

| Target | Day | Median ΔCt | Median ΔΔCt | Median RQ | Median Fold Change | P-value | Mean ΔCt | Mean ΔΔCt | Mean RQ | Mean Fold Change |
|---|---|---|---|---|---|---|---|---|---|---|
| TLR7 | 3 | 14.61 | 0.02 | 0.989 | −1.011 | 0.5166 | 13.71 | −1.18 | 2.27 | 2.27 |
| TLR7 | 8 | 15.91 | 1.31 | 0.402 | −2.847 | 0.1782 | 16.17 | 1.28 | 0.41 | −2.43 |
| TLR7 | 15 | 17.04 | 2.45 | 0.183 | −5.542 | 0.0018 | 17.91 | 3.02 | 0.12 | −8.11 |
| TLR9 | Pre | 14.57 | 0.00 | 1.000 | 1.000 | — | 14.93 | 0.00 | 1.00 | 1.00 |
| TLR9 | Post | 14.76 | 0.19 | 0.879 | −1.137 | 0.9416 | 14.88 | −0.06 | 1.04 | 1.04 |
| TLR9 | 3 | 14.89 | 0.32 | 0.801 | −1.248 | 0.3711 | 13.39 | −1.55 | 2.92 | 2.92 |
| TLR9 | 8 | 16.55 | 1.97 | 0.255 | −3.925 | 0.3668 | 15.71 | 0.78 | 0.58 | −1.72 |
| TLR9 | 15 | 17.20 | 2.63 | 0.162 | −6.175 | 0.0237 | 17.20 | 2.27 | 0.21 | −4.82 |

The P-value of Table 5 is the median, comparing the value at each time point with the "pre-prophylaxis treatment" sample. Similarly, the Fold Change is the derived as the median ΔCt or as the mean ΔCt. The "pre" and "post" entries refer to the Day 1 blood samples taken, respectively, before and after the dental prophylaxis.

Prior to dental intervention, these expression levels were higher than they were after the cats' oral health improved. The data suggest that there were no immediate responses to prophylaxis; i.e., there was very little change from the pre- to post-prophylaxis time points, but the expression levels of each of the pattern recognition receptors dropped to below baseline (pre-prophylaxis) levels by the end of the study. Only MYD88 did not show a significant, or near significant reduction fourteen days after treatment.

In this study, the expression of TLR1, TLR4, TLR7, TLR9, TLR10, and NOD1 showed a significant response to periodontal disease intervention on day 15, i.e., 14 days after the dental prophylaxis. MYD88 showed a numerical response that paralleled the others, but was not statistically significant. After day 3, the expression levels of all of the pattern recognition receptors dropped, ultimately to levels lower than they were at base line. These data further indicate that pattern recognition receptors are useful as systemic markers of periodontal disease, status, for example but not limited to, bacteremia associated with periodontal disease or arising from "leakage" of oral pathogens into the body during, e.g., professional dental cleaning.

The data provided above, demonstrating that expression levels of pattern recognition receptors (TLR1, TLR3, TLR4, TLR7, TLR9, TLR10, MYD88, and NOD1) responded to oral care therapy, e.g., periodontal disease intervention, establish that there is in fact a causal link between oral health and systemic health.

Example 2

Second Intervention Study

This second intervention study was also designed to determine whether or not the expression levels of the pattern recognition receptors (TLR1, TLR3, TLR4, TLR7, TLR9, TLR10, MYD88, and NOD1) would respond to oral care therapy, e.g., periodontal disease intervention, and thereby establish a causal link between oral health and systemic health.

A total of 48 cats with severe periodontal disease where randomized into two groups, with Group I containing 30 cats and Group II containing 18 cats. Pre-existing dental disease was evaluated using a semi-quantitative visual scoring system graded on a scale of from 0 to 4. The two groups were compared prior to treatment to ensure that there was no significant difference in apparent severity. Cats were maintained on their staple canned diet throughout the experimental period in controlled conditions.

Initially, blood samples were taken from all cats to assess pattern recognition receptor expression prior to intervention, i.e., at Day −16. Sixteen days after this initial blood collection, periodontal disease treatments were performed on the 30 cats of the Test Group (Group I). Treatment of the periodontal disease of the control cats was performed later in the study and their pattern recognition receptor expression levels provided reference ("untreated") values. All cats received amoxicillin/clavulanate immediately pre-op but nothing post-op (except for 1 cat, which required additional treatment with buprenorphine and amoxicillin/clavulanate, before being returned to the study).

All cats received buprenorphine (40 μg/kg s/c) immediately pre-op, which was carried out under standard conditions. None of the cats were administered non-steroidal anti-inflammatory drugs at any point during this study.

Blood samples were also collected 16, 45, 90, and 180 days after treatment in the Test Group (Group I) and 16, 45, and 90 days after treatment in the Control Group (Group II). All blood samples were collected into PAXgene blood RNA tubes under standard conditions and stored frozen until analysis. These blood samples were used to assess the expression levels of TLR1, TLR4, TLR7, TLR9, TLR10, MYD88, and NOD1 by qRT-PCR, according to the methods described above.

The PCR analysis was carried out twice. In the initial analysis, pattern recognition receptor expression levels for all the available RNA samples for both the Test and Control groups were assessed and the results blended at baseline. However, in this initial study, only the available Test Group RNA samples were assessed at the additional time points. The second analysis was run and focused specifically on the Day −16 and Day +16 time points. Again the pattern recognition receptor expression levels for the available RNA samples from both the Test and Control Groups were assessed and the results blended at baseline. However, the Day +16 Test and Control Group pattern recognition receptor expression levels were kept separate, with the expectation that this method of analysis would differentiate between pattern recognition receptor expression levels that changed as a function of treatment (i.e., Test Group cats), and would also identify any changes that may have occurred as a function of time rather than treatment (i.e., Control Group cats). In addition, the second analysis used a different "housekeeping" gene than in the first analysis to reduce the variability of the assay.

Gingivitis scores for the two groups (Test and Control) of cats averaged 2.2 of a possible 4, indicating significant gingivitis. Initial analysis of pattern recognition receptor expression levels from all of the cats as baseline, but only the Test Group of cats post-prophylaxis showed a significant decrease as a function of treatment in all but TLR7. In all cases there was a numerical decrease in pattern recognition receptor expression levels at the first data point post-prophylaxis (Day +16). However, after the Day 45 time point, all pattern recognition receptor expression levels returned to lower levels, ending at levels significantly below the baseline values at Day 180, as indicated in Table 6, below.

TABLE 6

| Target | Day | Average ΔCt | Median ΔCt | ΔΔCt | RQ | Fold Change | P-value |
|---|---|---|---|---|---|---|---|
| MYD88 | −16 | 5.1 | 4.9 | 0.00 | 1.00 | 1.00 | — |
| MYD88 | 16 | 6.9 | 7.4 | 2.5 | 0.2 | −5.8 | 0.0497 |
| MYD88 | 45 | 4.8 | 4.3 | −0.5 | 1.4 | 1.4 | 0.7283 |
| MYD88 | 90 | 5.1 | 5.6 | 0.7 | 0.6 | −1.7 | 0.9559 |
| MYD88 | 180 | 7.4 | 7.5 | 2.7 | 0.2 | −6.3 | 0.0033 |
| NOD1 | −16 | 9.4 | 9.3 | 0.00 | 1.00 | 1.00 | — |
| NOD1 | 16 | 11.7 | 11.8 | 2.5 | 0.2 | −5.6 | 0.0156 |
| NOD1 | 45 | 9.4 | 9.4 | 0.1 | 1.0 | −1.0 | 0.9677 |
| NOD1 | 90 | 9.6 | 9.8 | 0.4 | 0.8 | −1.3 | 0.8297 |
| NOD1 | 180 | 12.3 | 12.0 | 2.6 | 0.2 | −6.1 | 0.0004 |
| TLR1 | −16 | 2.3 | 2.4 | 0.00 | 1.00 | 1.00 | — |
| TLR1 | 16 | 4.2 | 4.9 | 2.5 | 0.2 | −5.5 | 0.0353 |
| TLR1 | 45 | 3.0 | 2.9 | 0.4 | 0.7 | −1.3 | 0.3939 |
| TLR1 | 90 | 3.1 | 3.3 | 0.9 | 0.5 | −1.8 | 0.3582 |
| TLR1 | 180 | 5.1 | 4.5 | 2.1 | 0.2 | −4.2 | 0.0036 |
| TLR10 | −16 | 7.8 | 7.2 | 0.00 | 1.00 | 1.00 | — |
| TLR10 | 16 | 9.1 | 9.7 | 2.5 | 0.2 | −5.6 | 0.1510 |
| TLR10 | 45 | 7.9 | 8.4 | 1.2 | 0.4 | −2.4 | 0.8763 |
| TLR10 | 90 | 8.3 | 8.9 | 1.7 | 0.3 | −3.3 | 0.5327 |
| TLR10 | 180 | 9.6 | 9.0 | 1.8 | 0.3 | −3.6 | 0.112 |
| TLR4 | −16 | 5.3 | 5.6 | 0.00 | 1.00 | 1.00 | — |
| TLR4 | 16 | 8.1 | 8.7 | 3.2 | 0.1 | −8.9 | 0.0044 |
| TLR4 | 45 | 5.1 | 5.4 | −0.1 | 1.1 | 1.5 | 0.9087 |
| TLR4 | 90 | 5.4 | 6.0 | 0.4 | 0.8 | −1.3 | 0.8397 |
| TLR4 | 180 | 7.4 | 7.6 | 2.0 | 0.3 | −4.0 | 0.0160 |
| TLR7 | −16 | 8.8 | 9.0 | 0.00 | 1.00 | 1.00 | — |
| TLR7 | 16 | 10.2 | 10.9 | 1.9 | 0.3 | −3.6 | 0.1593 |
| TLR7 | 45 | 8.6 | 8.9 | −0.2 | 1.1 | 1.1 | 0.8069 |
| TLR7 | 90 | 8.9 | 9.0 | 0.0 | 1.0 | 1.0 | 0.8478 |
| TLR7 | 180 | 10.1 | 10.6 | 1.6 | 0.3 | −3.0 | 0.1030 |
| TLR9 | −16 | 8.6 | 8.4 | 0.00 | 1.00 | 1.00 | — |
| TLR9 | 16 | 10.7 | 11.3 | 2.9 | 0.1 | −7.5 | 0.0396 |
| TLR9 | 45 | 8.5 | 8.1 | −0.3 | 1.3 | 1.5 | 0.9717 |
| TLR9 | 90 | 8.9 | 8.7 | 0.2 | 0.9 | −1.2 | 0.7011 |
| TLR9 | 180 | 11.2 | 11.4 | 2.9 | 0.1 | −7.6 | 0.0018 |

Focusing on the on the early time points, it is apparent that there was a clear and significant decrease in most systemic pattern recognition receptor expression levels as a function of oral health intervention. This result is comparable to that obtained in the first intervention study described above.

Comparing only the pre- and post-prophylaxis time points, i.e., Day −16 and Day +16, for both the Test and Control Groups of cats in a reanalysis of this experiment using a different gene as reference provided results similar to those of the initial analysis described above. The expression levels of all of the pattern recognition receptors were numerically reduced from baseline for the Test Group cats, but were unchanged for the Control Group cats (with the exception of TLR 10). The changes for the Test Group cats were statistically significant for TLR1 and TLR7. TLR10 expression levels were down-regulated for both the Test Group cats and the Control Group cats, indicating an effect of time but not of treatment for expression of this pattern recognition receptor.

The data provided above in Example 3, again demonstrate that expression levels of pattern recognition receptors (TLR1, TLR3, TLR4, TLR7, TLR9, TLR10, MYD88, and NOD1) respond to oral care therapy, e.g., periodontal disease intervention, further reinforcing the existence of a causal link between oral health and systemic health.

The collected data obtained and set forth above demonstrate that (a) some pattern recognition receptor expression levels in cats with periodontal disease are significantly higher than in those same cats with good oral health, (b) communication exists between the oral cavity and the rest of the body, as evidenced by the up-regulation of pattern recognition receptor expression in cats with periodontal disease, and (c) oral health intervention in the form of a complete dental prophylaxis attenuates a systemic consequence of oral disease. Because leakage of bacteria from the oral cavity into the rest of the body may be regular or continuous in diseased animals, it is likely to result in the regular or continuous up-regulation of pattern regulation receptor expression. This in turn may initiate a more comprehensive immune response, contributing to a chronic systemic inflammatory burden.

We claim:

1. A method for treating chronic systemic inflammation in a companion animal in need thereof and afflicted with an oral health condition, the method comprising:
   identifying the companion animal in need thereof and afflicted with the oral health condition, wherein identifying the companion animal in need thereof comprises:
      determining a first expression level of a first pattern recognition receptor in a blood sample from the companion animal;
      comparing the first expression level to a control first expression level of the first pattern recognition receptor;
      measuring an increase of at least a two fold change in the expression of the first expression level relative to the control first expression level, wherein the increase of at least a two fold change in the expression of the first expression level relative to the control first expression level indicates the companion animal having poor systemic health; and
   treating the companion animal by subjecting the animal to a dental prophylaxis, wherein treating the companion animal decreases expression of the first pattern recognition receptor,
   wherein the companion animal is afflicted with an oral health condition;
   wherein the oral health condition is selected from the group consisting of gingivitis, periodontitis, dental plaque, dental tartar, resorptive tooth lesion, mobile tooth, attachment loss, and gingival recession; and
   wherein the first pattern recognition receptor is Toll Like Receptor 10 (TLR10).

2. The method of claim 1, further comprising determining an expression level of at least one second pattern recognition receptor in the blood sample from the companion animal; and
   comparing the second expression level of the second pattern recognition receptor to a control second expression level of the second pattern recognition receptor;
   wherein the control second expression level is determined in healthy control animals not afflicted with the oral health condition;
   wherein good systemic health is indicated by the subject second expression level being equal to or less than the control second expression level and poor systemic health is indicated by the second expression level being greater than the control second expression level.

3. The method of claim 2, wherein the at least one second pattern recognition receptor is selected from the group consisting of Toll Like Receptor 1 (TLRI), Toll Like Receptor 3 (TLR3), Toil Like Receptor 7 (TLR7), Toll Like Receptor 9 (TLR9), Toll Like Receptor 10 (TLR10), myeloid differentiation primary response gene 88 (MyD88), and Nucleotide Binding oligomerization domain containing protein 1 (NOD1).

4. The method of claim 1, wherein the companion animal is a feline.

5. The method of claim 1, wherein the companion animal is a canine.

6. The method of claim 1, wherein the first expression level and the control first expression level are determined using quantitative real time, polymerase chain reaction analysis (qRT-PCR) of mRNA.

7. The method of claim 2, wherein the second expression level and the control second expression level are determined using quantitative real time, polymerase chain reaction analysis (qRT-PCR) of mRNA.

8. The method of claim 6, wherein calculation of the first expression level and the control first expression level comprise normalization of data relative to that of a calibrator mRNA.

9. The method of claim 7, wherein calculation of the second expression level and the control second expression level comprise normalization of expression data relative to that of a calibrator mRNA.

10. The method of claim 1, wherein the poor systemic health is indicated by the first expression level being at least a three fold increase relative to the control first expression level.

11. The method of claim 1, wherein the dental prophylaxis is configured to ameliorate periodontal disease.

12. A method for treating systemic health of a companion animal in need thereof and afflicted with an oral health condition, the method comprising:
   identifying the companion animal in need thereof and afflicted with the oral health condition, wherein identifying the companion animal in need thereof comprises:
      determining a first expression level of a first pattern recognition receptor in a blood sample from the companion animal at a first time point, wherein the first pattern recognition receptor is Toll Like Receptor 10 (TLR10);
      determining a second expression level of the first pattern recognition receptor in a blood sample from the companion animal at a second time point subsequent to the first time point;
      measuring an increase of at least a two fold change in the expression of the first expression level relative to the second expression level, wherein the increase of at least a two fold change in the expression of the first expression level relative to the second expression level indicates the companion animal as having poor systemic health; and
   treating the companion animal by subjecting the animal to a therapy of the oral health condition, wherein treating the companion animal decreases expression of the first pattern recognition receptor.

13. The method of claim 1, further comprising measuring a decrease in the expression of the first pattern recognition receptor relative to the first expression level of the first pattern recognition receptor after treating the companion animal by subjecting the animal to the dental prophylaxis, wherein the dental prophylaxis comprises dental cleaning.

14. The method of claim 12, wherein the therapy of the oral health condition comprises dental cleaning.

15. The method of claim 13, wherein the method consists of:
- identifying the companion animal in need thereof and afflicted with the oral health condition, wherein identifying the companion animal in need thereof consists of:
  - determining the first expression level of the first pattern recognition receptor in the blood sample from the companion animal;
  - comparing the first expression level to the control first expression level of the first pattern recognition receptor; and
  - measuring the increase of at least a two fold change in the expression of the first expression level relative to the control first expression level;
- treating the companion animal by subjecting the animal to the therapy of the oral health condition; and
- measuring the decrease in the expression of the first pattern recognition receptor relative to the first expression level of the first pattern recognition receptor after treating the companion animal by subjecting the animal to the dental prophylaxis, wherein the dental prophylaxis comprises dental cleaning.

16. The method of claim 1, wherein the control first expression level is determined in healthy control animals not afflicted with the oral health condition.

17. The method of claim 1, wherein the first expression level of the first pattern recognition receptor in the blood from the companion animal is determined prior to or immediately after treating the companion animal.

18. The method of claim 1, wherein the method does not include administering a non-steroidal anti-inflammatory drug (NSAID) to the companion animal in need thereof.

19. The method of claim 1, wherein the method consists of:
- identifying the companion animal in need thereof and afflicted with the oral health condition, wherein identifying the companion animal in need thereof consists of:
  - determining the first expression level of the first pattern recognition receptor in the blood sample from the companion animal;
  - comparing the first expression level to the control first expression level of the first pattern recognition receptor; and
  - measuring the increase of at least a two fold change in the expression of the first expression level relative to the control first expression level; and
- treating the companion animal by subjecting the animal to the therapy of the oral health condition.

20. A method for treating chronic systemic inflammation in a companion animal in need thereof and afflicted with an oral health condition, the method consisting of:
- identifying the companion animal in need thereof and afflicted with the oral health condition, wherein identifying the companion animal in need thereof consists of:
  - determining an expression level of a first pattern recognition receptor in a blood sample from the companion animal;
  - comparing the expression level of the first pattern recognition receptor to a control expression level of the first pattern recognition receptor; and
  - measuring at least a two fold increase in the expression level of the first pattern recognition receptor relative to the control expression level; and
- treating the companion animal by subjecting the animal to a dental prophylaxis, wherein treating the companion animal decreases expression of the first pattern recognition receptor,
- wherein the companion animal is afflicted with an oral health condition; and
- wherein the first pattern recognition receptor is Toll Like Receptor 10 (TLR10).

21. The method of claim 20, wherein the at least a two fold increase in the expression level of the first pattern recognition receptor relative to the control expression level indicates the companion animal having poor systemic health.

22. The method of claim 21, wherein the companion animal is a feline.

23. The method of claim 22, wherein the control expression level is determined in healthy control animals not afflicted with the oral health condition.

24. The method of claim 23, wherein the expression level of the pattern recognition receptor in the blood from the companion animal is determined prior to treating the companion animal.

25. The method of claim 20, wherein the expression level of the pattern recognition receptor in the blood from the companion animal is determined prior to treating the companion animal.

* * * * *

UNITED STATES PATENT AND TRADEMARK OFFICE
CERTIFICATE OF CORRECTION

PATENT NO. : 10,876,161 B2
APPLICATION NO. : 14/654272
DATED : December 29, 2020
INVENTOR(S) : Samer Al-Murrani et al.

Page 1 of 1

It is certified that error appears in the above-identified patent and that said Letters Patent is hereby corrected as shown below:

In the Specification

In Column 11, Line 3, delete "OCT" and insert -- ACT --, therefor.

In the Claims

In Column 55, Line 63, in Claim 3, delete "Toil" and insert -- Toll --, therefor.

Signed and Sealed this
Ninth Day of March, 2021

Drew Hirshfeld
*Performing the Functions and Duties of the
Under Secretary of Commerce for Intellectual Property and
Director of the United States Patent and Trademark Office*